United States Patent [19]
Ronald et al.

[11] Patent Number: 5,977,434
[45] Date of Patent: *Nov. 2, 1999

[54] PROCEDURES AND MATERIALS FOR CONFERRING DISEASE RESISTANCE IN PLANTS

[75] Inventors: Pamela C. Ronald; Guo-Liang Wang; Wen-Yuang Song; Veronique Szabo, all of Davis, Calif.

[73] Assignee: The Regents of the University of California, Oakland, Calif.

[ * ] Notice: This patent is subject to a terminal disclaimer.

[21] Appl. No.: 08/587,680

[22] Filed: Jan. 17, 1996

Related U.S. Application Data

[63] Continuation-in-part of application No. 08/567,375, Dec. 4, 1995, and a continuation-in-part of application No. 08/475,891, Jun. 7, 1995, Pat. No. 5,859,339, which is a continuation-in-part of application No. 08/373,375, Jan. 17, 1995, abandoned
[60] Provisional application No. 60/004,645, Sep. 29, 1995.

[51] Int. Cl.$^6$ .............................. C12N 15/82; C12N 5/04; C12N 15/29; A01H 5/00
[52] U.S. Cl. ..................... 800/278; 435/69.1; 435/70.1; 435/468; 435/471; 435/410; 435/411; 435/418; 435/419; 435/320.1; 536/23.1; 536/23.6; 800/278; 800/279; 800/295; 800/317.4
[58] Field of Search .............................. 435/172.3, 320.1, 435/69.1, 70.1, 468, 471, 410, 411, 418, 419; 536/23.6, 23.1; 800/205, 278, 279, 295, 317.4

[56] References Cited

FOREIGN PATENT DOCUMENTS

| | | |
|---|---|---|
| 098656 | 4/1992 | Japan . |
| WO 93/0779 | 4/1993 | WIPO . |

OTHER PUBLICATIONS

Taniguchi et al. Structure of genes that encode isozymes of aspartate aminotransferase in *Panicum miliaceum* L., a C4 plant. Plant Molecular Biology. 26:723–734, Nov. 1994.

Ronald, Pamela C., et al. (1992) "Genetic and physical analysis of the rice bacterial blight resistance locus, Xa21", *Mol. Gen. Genet.*, 236:113–120.

Abenes, M.L.P., et al. (1994) "Orientation and integration of the classical and molecular genetic maps of chromosome 11 in rice", *Euphytica*, 76:81–87.

Wang, Guo–Liang, et al. (1995) "Construction of a rice bacterial artificial chromosome library and identification of clones linked to the Xa–21 disease resistance locus", *The Plant Journal*, 7(3):525–533.

Jiang, J., et al. (1995) "Metaphase and interphase fluorescence in situ hybridization mapping of the rice genome with bacterial artificial chromosomes", *Proc. Natl. Acad. Sci USA*, 92(10):4487–4491.

Song, Wen–Yuan, et al. (1995) "A receptor kinase–like protein encoded by the rice disease resistance gene, Xa21", *Science*, 270:1804–1806.

Johal, Gurmukh S., et al (1992) "Reductase Activity Encoded by the HM1 Disease Resistance Gene in Maize", *Science*, 258:985–987.

Martin, Gregory B., et al. (1993) "Map–Based Cloning of a Protein Kinase Gene Conferring Disease Resistance in Tomato", *Science*, 262:1432–1436.

Bent, Andrew F., et al. (1994) "RPS2 of *Arabidopsis thaliana*: A Leucine–Rich Repeat Class of Plant Disease Resistance Genes", *Science*, 265:1856–1860.

Jones, David A., et al. (1994) "Isolation of the Tomato Cf–9 Gene for Resistance to *Cladosporium fulvum* by Transposon Tagging", *Science*, 266:789–793.

*Primary Examiner*—Lynette F. Smith
*Assistant Examiner*—Ousama M-Faiz Zaghmout
*Attorney, Agent, or Firm*—Townsend and Townsend & Crew LLP

[57] ABSTRACT

The present invention provide nucleic acids encoding polypeptides which confer resistance to Xanthomonas spp. The nucleic acids can be used to produce transgenic plants resistant to the pathogen.

45 Claims, 7 Drawing Sheets

| | | | |
|---|---|---|---|
| RICE | pB806 | \|Sx\|xx\|xx\|xx\|x\|xx\|x\|S\|x\| | 23x24 |
| YEAST | adcyc | \|xx\|xx\|xx\|xx\|x\|xx\|x\|xxL | 28x23 |
| FLY | TO11 | \|xx\|FxHxxNLxxLxLxxNxLxxL | 30x24 |
| ARAB | RLK5 | \|xx\|xx\|xx\|xx\|x\|\|x\|x\|S\|x\| | 21x24 |
| SNAP | Fil2 | \|xx\|xx\|xx\|xS\|x\|\|x\|x\|x\|xI | 10x24 |
| TOMATO | PGIP | \|xxxxx\|xx\|xx\|x\|\|x\|x\|x\|xI | 10x24 |
| TOMATO | CF9 | \|Sx\|xx\|xx\|xx\|x\|\|xxx\|x\|xI | 28x24 |

*FIG. 1.*

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
　　　　(A) LENGTH: 6256 base pairs
　　　　(B) TYPE: nucleic acid
　　　　(C) STRANDEDNESS: single
　　　　(D) TOPOLOGY: linear (ii) MOLECULE TYPE: DNA (genomic)

(ix) FEATURE:
　　　　(A) NAME/KEY: CDS
　　　　(B) LOCATION: join(1648..4383, 5178..5513)
　　　　(D) OTHER INFORMATION: /product= "RRK-F"
　　　　　　/note= "Xa21 Xanthomonas spp. disease
　　　　　　resistance gene RRK-F from rice (Oryza
　　　　　　sativa)"

(xi) SEQUENCE DESCRIPTION: SEQ ID NO:1:

AAGCTTTCTA AATTATTTAA CTCTAAGTCT GTTATTATCC CCAAGTACAT CATCATCATA　　60

CATAATATTT CATATTCACG ACATCCTTAA GCTAGATGCT TTTGGCCATT CTCTTATCTT　　120

TTTAAAGAAA TTCTCTCCCA ATTAAGATGA GAGTGTCTTC TAGCAATTTG CCAGTTTTTA　　180

CAATGTCTTT GAGTCCTCAC ACATTTTCAT GATGTTACCA ATAAATTACG GACGCCGTGT　　240

TTAGTTCTAA AGTTTTTCTT CAAACTTACA ACTTTTCAAT CGCATCAAAA CTTTCTCCTA　　300

CACACACAAA CTTTCAACTT TTCCATCACA TCGTTCCAAT TTCAACCAAA CTTCCAATTT　　360

```
TGGTATGAAC TAAACACAGC CGAAAACAAA ATCTGTGTGT TATGGCCCTG TTTAGATTCT    420

AACTTTTCCA TTACATCAAA CTTTCCTACA TACACGAACT TTCAACTTTT CCGTCACATC    480

GTTTCAATTT TTTAAAACTT CCATTTTTAA CGTGGAACTA AACACAACCT ATATAACGGA    540

ATTTGTCAAA AACTCAATGG TGAAAGTCAC ACCTCACAGG AAGGGCGCGC TCTAGTCAAG    600

ACATCATTAA ACAGGTACAC AGGTTGTACT AGCTTGTCAT GTTTATCTTG CGTCTGCGAG    660

ACGTAAATCC ATGCCAAACA AAAGTGCTTC TATAGAGATA TCATAAGGAT ATGGTTTGGG    720

GCCATATCCA ACTGCTCAGG AGAGATCTCG TTCGGAGGTG AGGTTAGATG TTCACCTCTC    780

CACACATAAC GAAGGCGATC TTCTTCGCAT ATGATTAGGC ATTAGATAAA ATAACCTTAA    840

AAAATAAATC AATATGATTT TTTTAGAAAA AAATTATATA CACTAAGTAT AAGCATTGTC    900

AAGGAGGAAG AAACACACAC TCCCATATAG AGAGATAGAA ACATAGCTAT AGGTAGTGTC    960

ACTGAGTATT TTCCATCACG CATATCCATA TAAAATTAGG GGGTGTTACA TCCATAGGTG   1020

TAAAGTTTTG GCATGTTATA TCGAGTATTA CGTAGAATGC CGTATTAGGT GTCCGGGCAC   1080

TAATAAAAAA ATAATTACAG AATCCGTTAG TAAACCGCGA GATAAATTTA TTAAGCCTAA   1140

TTAATCCCAT CATTAACAAA TGTTTACCGT AGCACCACAT TGTCAAATCA TGGAGCAATT   1200

AGGTTTAAAA GATTCGTCTC GCAAATTAGT CATAATCTGT GCAATTAGTT ATTTTTAGAC   1260

TATATTTAAG ACTTCGTACA GGTGTTCAAA CGTTCGATGT GACATGGTGC AAAATTTTAG   1320

GGTGTCATCT AGACACTCCC TTAATTAGAA AGTTAGGAAG AGGCGGTAAA GAACGCAGCA   1380

TGACTGAAAC TTTGAAAATT TGATAAGGTA CACCAACTGG AGTATCTTTT ATTTTCATTG   1440

AAGACTTTGA CCAGAAGAGC TTGACCCGTT TTTCTTGGAG TAGCCAGTAA TGTTTCATTC   1500

TTTTCCTTTT GCTGGGACTT CTTTTTATTT TTTTTGACAG GAGCCATTTG TTGGGACTTG   1560

GGATCCCTTT ACTGTTATAG GACCAGTGCT TGAATCCAAA CACTGCATTG ATCAGCTCAG   1620

CTCATTGTAG CGCACTCCTC CGCATGCATG GCGAGATCAC CAACGTCGGT CATGATCTCT   1680

TCTTTGCTGC TGCTGCTGTT GATCGGCCCA GCGAGCAGTG ACGATGATGC TGCTGCTGCT   1740

GCTGCTCGTA CCAGTACAGG CGGCGTCGCG GCGACGAACT CGCGCTGCTC TCTTTCAAGT   1800

CATCCCTGCT ACACCAGGGG GGCTTGTACG CTGGCATCTT GGAACACGTC CGGCCACGGC   1860

CAGCACTGCA CATGGGTGGG TGTTGTGTGC GGCCGCGCGC GCCGGCACCC ACACAGGGTG   1920

GTGAAGCTGC TGCTGCGCTC GTCCAACCTG TCCGGGATCA TCTCGCCGTC GCTGGGCAAC   1980

CTGTCCTTCC TCAGGGAGCT GGACCTCAGC GACAACTACC TCTCCGGCGA GATACCACCG   2040

GAGCTCAGCC GTCTCAGCAG GCTTCAGCTG CTGGAGCTGA GCGGTAACTC CATCCAAGGG   2100

AGCATCCACG CGGCCATTGG AGCATGCACC AAGTTGACAT CGCTAGACCT CAGCCACAAC   2160

CAACTGAGAT TGGTGCCAGC TGAAACATCT CTCGAATTTG TACCTTCACA CCAATGGTTA   2220

TGTCAGGAGA GATTCCATCT GATTTTGGGC AATCTCACTA CGCCTTCAGT ATTTGATTTG   2280

ACCTGCAACA GATTATCACG GAGCTATACC TTCATCGCTA GGGCAGCTCA GCAGCAGTCT   2340

ATTGACTATG AATTTTGTGC TACGAACAAT CTAACTGGCA TGATCCCCAA TTCTATCTGG   2400

AACCTTTCGT CTCTAGCAGC GTTTAGCTGT CAAGCGAAAA ACAAGCTAGG TGGTATGATC   2460

CCTACAAATG CATTCAAAAC CCTTCACCTC CTCGAGGTGG TAGATATGGG CACTAACCGA   2520

TTCCATGGCA AAATCCCTGC CTCAGTTGCT AATGCTTCTC ATCTGACACG GCTTCAGATT   2580

GATGGCAACT TGTTCAGTGG AATTATCACC TCGGGGTTTG GAAGGTTAAG AAATCTCACA   2640

ACACTGTATC TCTGGAGAAA TTTGTTTCAA ACTAGAGAAC AAGAAGATTG GGGGTTCATT   2700

TCTGACCTAA CAAATTGCTC CAAATTACAA ACATTGGACT TGGGAGAAAA TAACCTGGGG   2760
```

```
GGAGTTCTTC CTAATTCGTT TTCCAATCTT TCCACTTCGC TTAGTTTTCT TGCACTTGAT    2820

TTGAATAAGA TCACAGGAAG CATTCCAAAG GATATTGGCA ATCTTATTGG CTTACAACAT    2880

CTCTATCTCT GCAACAACAA TTTCAGAGGG TCACTTCCAT CATCGTTGGG CAGGCTTAGA    2940

AACTTAGGCA TTCTAGTCGC CTACGAAAAC AACTTGAGCG GTTCGATCCC ATTGGCCATA    3000

GGAAATCTTA CTGAACTTAA TATCTTACTG CTCGGCACCA ACAAATTCAG TGGTTGGATA    3060

CCATACACAC TCTCAAACCT CACAAACTTG TTGTCATTAG GCCTCTCGCA CCTCGCACCA    3120

CAATCAGGGT TGGATACCTA CACATCTCAA CCTCACAACT GTGTCATAGC CTTCACTATA    3180

CCTAGTGGGT CCCAAATACC CCAGGTGAAA TTAATTCAAA TAGTCCAAAC ACCTATCAAA    3240

AAGATGATCA ATGTATCAAA AAATACACTT GGAGGGATCA GATACCCACA AGAAATAGGG    3300

CATCTCAAAA ATCTAGTAGA ATTCATGCAG AATCGAATAG ATATCAGTAA AATCCCTAAC    3360

ACGCTTGGTG ATTGCCAGCT CTTACGGTAT CTTTATCTGC AAAATAATTT GTTATCTGGT    3420

AGCATCCCAT CAGCCTTGGG TCAGCTGAAA GGTCTCGAAA CTCTTGATCT CTCAAGCAAC    3480

AATTTGTCAG GCCAGATACC CACATCCCTT AGCAGATATT ACTATGCTTC ATTCCTTGAA    3540

CCTTTCTTTC AACAGCTTTG TGGGGAAGT GCCAACCATT GCGTGCTTTC GCAGATGCAT    3600

CCGGGATCTC AATCCAAGGC AATGCCAAAC TCTGTGGTGG AATACCTGAT CTACATCTGC    3660

CTCGATGTTG TCCCATTACT AGAGAACAGA AAGCATTTTC CAGCTCTACC TATTTCTGTT    3720

TCTCTGGTCG CAGCACTGGC CATCCTCTCA TCACTCTACT TGCTTATAAC CTGGAACAAG    3780

AGAACTAAAA AGGGAGCCCC TTCAAGAACT TCCATGAAAA GCCACCCATT GGTCTCTTAT    3840

CCGCAGTTGG TAAAAGCAAC AGATGGTTTC GCGCCGACCA ATTTGTTGGG TTCTGGATCA    3900

TTTGCCTCAG TATACAAACG AAAGCTTGAA ATCCTAAGG CACTCAAGAG TTTCACTGCC    3960

GAATGTGAAG CACTACGAAA TATGCGACAT CGAAATCTTG TCAAGATAGT TACAATTTGC    4020

TCGAGCATTG ATAACAGAGG GAACGATTTC AAAGCAATTG TGTATGACTT CATGCCCAAC    4080

GGCAGTCTGG AAGATTGGAT ACACCCTGAA ACAAATGATC AAGCAGACCA GAGGCACTTG    4140

AATCTGCATC GAAGAGTGAC CATACTACTT GATGTTGCCT GTGCATTGGA CTATCTTCAC    4200

CGCCATGGCC CTGAACCTGT TGTACACTGT GATGTTAAAT CAAGCAATGT GCTGTTAGAT    4260

TCTGATATGG TAGCGCATGT TGGAGATTCT GGGCTTGCAA GAATACTTGT TGATGGGACC    4320

TCATTGATAC AACAGTCAAC AAGCTCGATG GGATTTAGAG GGACAATTGG CTATGCAGCA    4380

CCAGGTCAGC AAGTCCTTCC AGTATTTTGC ATTTTCTGAT CTCTAGTGCT ATATGAAATA    4440

GTTTTTACCT CTAGTGAAAC TGATGGAGAA TATAAGTAAT TAATTGAACT AATTAAATTG    4500

CACAAAAATA AGATTATTTG CCATATCTAT TCAGATGCTA AATATAGCTA GTTCATAGAG    4560

GTACATATTT TTTTTATATA GGAATCTAGA GCTACTACAC ACTCAAATCA AATTATGGGT    4620

GTTTTCTGCT CTACACTGCA ATATGAAATG ATTATCAGAA GGATCAAATT TGAGTAAATT    4680

TGTCAATTCT ACATTTAAGA AACACTTTTT TTTGTATGTA CTAGTTATTA CAATTTTTA    4740

TTTCAAGAAC TTGCATTGAC CATGAAAAGT ACTTGGTACT ACTTCTAATT CCCACATGGA    4800

GGTGGTGAAA ATAATATAGA TACAAAAACG AAGTATCATA TGTTGTGTGA TATACTATAA    4860

TCACAATGAA CACAAACAGG ATTCGTACAA AAGTAATTGG CCATCATAGC AACTGATTGC    4920

TTGGGGTAAC TGTATAGCAC AATCATACCA AATTTCTTTA GATATGTATT TGTAAATTAG    4980

ATTCTTAAAG TTAAATATGA AATTTCATTG GTATTTATGT TTCTTTATAT AATAAAAATT    5040

AATCCAACCT TTACATCTAC CATTTGTCCA GCCATCCTTG TTATTTGTGA TATTTAACAC    5100

GTAATTTTAC ATAATTATAC ATCCAAGTTC TTTTTATTTA ACACTGGAAA TTTGAAATCG    5160
```

| | |
|---|---|
| TATTTCCTAC TCAAACAGAG TATGGCGTCG GGCACATTGC ATCAACACAT GGAGATATTT | 5220 |
| ACAGCTATGG AATTCTAGTG CTGGAAATAG TAACCGGGAA GCGGCCAACT GACAGTACAT | 5280 |
| TCAGACCCGA TTTGGGCCTC CGTCAGTACG TTGAACTGGG CCTACATGGC AGAGTGACGG | 5340 |
| ATGTTGTTGA CACGAAGCTC ATTTTGGATT CTGAGAACTG GCTGAACAGT ACAAATAATT | 5400 |
| CTCCATGTAG AAGAATCACT GAATGCATTG TTTCGCTGCT TAGACTTGGG TTGTCTTGCT | 5460 |
| CTCAGGATTT SCCATTGAGT AGACGCCACC CGGAGATATC ACCGACGAAC TGAATGCCAT | 5520 |
| CAAACAGAAT CTCTCCGGAG TTGTTTCCAG TGTGTGAAGG TGCGAGCCTC GAATTCTGAT | 5580 |
| GTTATGTCTT GTAATGTTTT ATTGCCACTA GTCTTCAGAT TGGAATGCTC TTCCGATCAG | 5640 |
| ACTTCTTCAG TGGTATCTAC CACACGATCA CTAAAGTCAT CGTGGCTATT TCCTGATCCA | 5700 |
| GCATATCTGA TCATGCATGT TCTGTGTTTT ATACCTGTAT TTTACTCTGA ATTGCCACAC | 5760 |
| CTCAACCCTG CCTCTGTTTG TTTGGCATAC AAAAGATAGT GATGAGTATA TTGTTTCAGG | 5820 |
| GGCTTCCTAG TTGGCGTGTG TGCTTACCGG CACGCACGCA GCCCGAGGGT GGGTTTCTTT | 5880 |
| TTTTTTCCAT TGTTATTCCG TTGCTTTTTT CCACCACGGT AGATTTTTTT TTTCTGGATT | 5940 |
| TCCATTTTTT CCGTTGTTTT TCTCTATCGC TTATGCTGGC GGATTTTTTT CCGTGGTTTT | 6000 |
| TTTTTCAAGA CGAGTATATC TAATGTAACT AACATGTTAC TTTTAGATAA CGATGGTTAT | 6060 |
| TAAGATAAGA TTTTTTTCTG GAAGATTTTT GTAAGTAAAT GGTAAAAAAT ATGGAAATGG | 6120 |
| AAACGGAAAT AGTTTTGCTG TTATACCGAT CGTTTCCATA TTTACCGTAT TCTTATAGAA | 6180 |
| ATTACCGTNT CTTATAATAT GGTAATTACC GTATTTCTAA ATATGTTGAT ATCGATTTTG | 6240 |
| CTATATATTT GTCGAC | 6256 |

(2) INFORMATION FOR SEQ ID NO:2:

(i) SEQUENCE CHARACTERISTICS:
  (A) LENGTH: 1023 amino acids
  (B) TYPE: amino acid
  (C) STRANDEDNESS:
  (D) TOPOLOGY: linear (ii) MOLECULE TYPE: protein (ix) FEATURE:
  (A) NAME/KEY: Protein
  (B) LOCATION: 1..1023
  (D) OTHER INFORMATION: /note= "Xa21 Xanthomonas spp. disease
   resistance polypeptide RRK-F from rice
   (Oryza sativa)"

(ix) FEATURE:
  (A) NAME/KEY: Modified-site
  (B) LOCATION: 1010
  (D) OTHER INFORMATION: /note= "Xaa = Leu when position 5471 of
   RRK-F = G or Phe when position 5471 of
   RRK-F = C"

(xi) SEQUENCE DESCRIPTION: SEQ ID NO:2:

```
Met Ala Arg Ser Pro Thr Ser Val Met Ile Ser Ser Leu Leu Leu Leu
1               5                  10                  15

Leu Leu Ile Gly Pro Ala Ser Ser Asp Asp Ala Ala Ala Ala
            20                  25                  30

Ala Arg Thr Ser Thr Gly Gly Val Ala Ala Thr Asn Ser Arg Cys Ser
            35                  40                  45

Leu Ser Ser His Pro Cys Tyr Thr Arg Gly Ala Cys Thr Leu Ala Ser
        50                  55                  60

Trp Asn Thr Ser Gly His Gly Gln His Cys Thr Trp Val Gly Val Val
65                  70                  75                  80
```

-continued

```
Cys Gly Arg Ala Arg Arg His Pro His Arg Val Val Lys Leu Leu Leu
                85                  90                  95

Arg Ser Ser Asn Leu Ser Gly Ile Ile Ser Pro Ser Leu Gly Asn Leu
                100                 105                 110

Ser Phe Leu Arg Glu Leu Asp Leu Ser Asp Asn Tyr Leu Ser Gly Glu
                115                 120                 125

Ile Pro Pro Glu Leu Ser Arg Leu Ser Arg Leu Gln Leu Leu Glu Leu
                130                 135                 140

Ser Gly Asn Ser Ile Gln Gly Ser Ile His Ala Ala Ile Gly Ala Cys
145                 150                 155                 160

Thr Lys Leu Thr Ser Leu Asp Leu Ser His Asn Gln Leu Arg Leu Val
                165                 170                 175

Pro Ala Glu Thr Ser Leu Glu Phe Val Pro Ser His Gln Trp Leu Cys
                180                 185                 190

Gln Glu Arg Phe His Leu Ile Leu Gly Asn Leu Thr Thr Pro Ser Val
                195                 200                 205

Phe Asp Leu Thr Cys Asn Arg Leu Ser Arg Ser Tyr Thr Phe Ile Ala
                210                 215                 220

Arg Ala Ala Gln Gln Ser Ile Asp Tyr Glu Phe Cys Ala Thr Asn
225                 230                 235                 240

Asn Leu Thr Gly Met Ile Pro Asn Ser Ile Trp Asn Leu Ser Ser Leu
                245                 250                 255

Ala Ala Phe Ser Cys Gln Ala Lys Asn Lys Leu Gly Gly Met Ile Pro
                260                 265                 270

Thr Asn Ala Phe Lys Thr Leu His Leu Leu Glu Val Val Asp Met Gly
                275                 280                 285

Thr Asn Arg Phe His Gly Lys Ile Pro Ala Ser Val Ala Asn Ala Ser
                290                 295                 300

His Leu Thr Arg Leu Gln Ile Asp Gly Asn Leu Phe Ser Gly Ile Ile
305                 310                 315                 320

Thr Ser Gly Phe Gly Arg Leu Arg Asn Leu Thr Thr Leu Tyr Leu Trp
                325                 330                 335

Arg Asn Leu Phe Gln Thr Arg Glu Gln Glu Asp Trp Gly Phe Ile Ser
                340                 345                 350

Asp Leu Thr Asn Cys Ser Lys Leu Gln Thr Leu Asp Leu Gly Glu Asn
                355                 360                 365

Asn Leu Gly Gly Val Leu Pro Asn Ser Phe Ser Asn Leu Ser Thr Ser
                370                 375                 380

Leu Ser Phe Leu Ala Leu Asp Leu Asn Lys Ile Thr Gly Ser Ile Pro
385                 390                 395                 400

Lys Asp Ile Gly Asn Leu Ile Gly Leu Gln His Leu Tyr Leu Cys Asn
                405                 410                 415

Asn Asn Phe Arg Gly Ser Leu Pro Ser Ser Leu Gly Arg Leu Arg Asn
                420                 425                 430

Leu Gly Ile Leu Val Ala Tyr Glu Asn Asn Leu Ser Gly Ser Ile Pro
                435                 440                 445

Leu Ala Ile Gly Asn Leu Thr Glu Leu Asn Ile Leu Leu Gly Thr
                450                 455                 460

Asn Lys Phe Ser Gly Trp Ile Pro Tyr Thr Leu Ser Asn Leu Thr Asn
465                 470                 475                 480

Leu Leu Ser Leu Gly Leu Ser His Leu Ala Pro Gln Ser Gly Leu Asp
                485                 490                 495

Thr Tyr Thr Ser Gln Pro His Asn Cys Val Ile Ala Phe Thr Ile Pro
                500                 505                 510
```

-continued

```
Ser Gly Ser Gln Ile Pro Gln Val Lys Leu Ile Gln Ile Val Gln Thr
        515                 520                 525
Pro Ile Lys Lys Met Ile Asn Val Ser Lys Asn Thr Leu Gly Gly Ile
        530                 535                 540
Arg Tyr Pro Gln Glu Ile Gly His Leu Lys Asn Leu Val Glu Phe Met
545                 550                 555                 560
Gln Asn Arg Ile Asp Ile Ser Lys Ile Pro Asn Thr Leu Gly Asp Cys
                565                 570                 575
Gln Leu Leu Arg Tyr Leu Tyr Leu Gln Asn Asn Leu Leu Ser Gly Ser
            580                 585                 590
Ile Pro Ser Ala Leu Gly Gln Leu Lys Gly Leu Glu Thr Leu Asp Leu
        595                 600                 605
Ser Ser Asn Asn Leu Ser Gly Gln Ile Pro Thr Ser Leu Ser Arg Tyr
        610                 615                 620
Tyr Tyr Ala Ser Phe Leu Glu Pro Phe Phe Gln Gln Leu Cys Gly Gly
625                 630                 635                 640
Ser Ala Asn His Cys Val Leu Ser Gln Met His Pro Gly Ser Gln Ser
                645                 650                 655
Lys Ala Met Pro Asn Ser Val Val Glu Tyr Leu Ile Tyr Ile Cys Leu
            660                 665                 670
Asp Val Pro Leu Leu Glu Asn Arg Lys His Phe Pro Ala Leu Pro
        675                 680                 685
Ile Ser Val Ser Leu Val Ala Ala Leu Ala Ile Leu Ser Ser Leu Tyr
        690                 695                 700
Leu Leu Ile Thr Trp Asn Lys Arg Thr Lys Lys Gly Ala Pro Ser Arg
705                 710                 715                 720
Thr Ser Met Lys Gly His Pro Leu Val Ser Tyr Pro Gln Leu Val Lys
                725                 730                 735
Ala Thr Asp Gly Phe Ala Pro Thr Asn Leu Leu Gly Ser Gly Ser Phe
            740                 745                 750
Ala Ser Val Tyr Lys Arg Lys Leu Glu Asn Pro Lys Ala Leu Lys Ser
        755                 760                 765
Phe Thr Ala Glu Cys Glu Ala Leu Arg Asn Met Arg His Arg Asn Leu
770                 775                 780
Val Lys Ile Val Thr Ile Cys Ser Ser Ile Asp Asn Arg Gly Asn Asp
785                 790                 795                 800
Phe Lys Ala Ile Val Tyr Asp Phe Met Pro Asn Gly Ser Leu Glu Asp
                805                 810                 815
Trp Ile His Pro Glu Thr Asn Asp Gln Ala Asp Gln Arg His Leu Asn
            820                 825                 830
Leu His Arg Arg Val Thr Ile Leu Leu Asp Val Ala Cys Ala Leu Asp
        835                 840                 845
Tyr Leu His Arg His Gly Pro Glu Pro Val Val His Cys Asp Val Lys
        850                 855                 860
Ser Ser Asn Val Leu Leu Asp Ser Asp Met Val Ala His Val Gly Asp
865                 870                 875                 880
Ser Gly Leu Ala Arg Ile Leu Val Asp Gly Thr Ser Leu Ile Gln Gln
                885                 890                 895
Ser Thr Ser Ser Met Gly Phe Arg Gly Thr Ile Gly Tyr Ala Ala Pro
            900                 905                 910
Glu Tyr Gly Val Gly His Ile Ala Ser Thr His Gly Asp Ile Tyr Ser
        915                 920                 925
Tyr Gly Ile Leu Val Leu Glu Ile Val Thr Gly Lys Arg Pro Thr Asp
```

```
                        930                 935                 940
Ser Thr Phe Arg Pro Asp Leu Gly Leu Arg Gln Tyr Val Glu Leu Gly
945                     950                 955                 960

Leu His Gly Arg Val Thr Asp Val Val Asp Thr Lys Leu Ile Leu Asp
                965                 970                 975

Ser Glu Asn Trp Leu Asn Ser Thr Asn Asn Ser Pro Cys Arg Arg Ile
            980                 985                 990

Thr Glu Cys Ile Val Ser Leu Leu Arg Leu Gly Leu Ser Cys Ser Gln
        995                 1000                1005

Asp Xaa Pro Leu Ser Arg Arg His Pro Glu Ile Ser Pro Thr Asn
    1010                1015                1020
```

(2) INFORMATION FOR SEQ ID NO:3:

(i) SEQUENCE CHARACTERISTICS:
        (A) LENGTH: 3921 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..2676, 3520..3918)
        (D) OTHER INFORMATION: /product= "Xa-21"

(xi) SEQUENCE DESCRIPTION: SEQ ID NO:3:

```
ATG ATA TCA CTC CCA TTA TTG CTC TTC GTC CTG TTG TTC TCT GCG CTG        48
Met Ile Ser Leu Pro Leu Leu Leu Phe Val Leu Leu Phe Ser Ala Leu
1               5                   10                  15

CTG CTC TGC CCT TCA AGC AGT GAC GAC GAT GGT GAT GCT GCC GGC GAC        96
Leu Leu Cys Pro Ser Ser Ser Asp Asp Asp Gly Asp Ala Ala Gly Asp
            20                  25                  30

GAA CTC GCG CTG CTC TCT TTC AAG TCA TCC CTG CTA TAC CAG GGG GGC       144
Glu Leu Ala Leu Leu Ser Phe Lys Ser Ser Leu Leu Tyr Gln Gly Gly
        35                  40                  45

CAG TCG CTG GCA TCT TGG AAC ACG TCC GGC CAC GGC CAG CAC TGC ACA       192
Gln Ser Leu Ala Ser Trp Asn Thr Ser Gly His Gly Gln His Cys Thr
    50                  55                  60

TGG GTG GGT GTT GTG TGC GGC CGC CGC CGC CGG CAC CCA CAC AGG           240
Trp Val Gly Val Val Cys Gly Arg Arg Arg Arg Arg His Pro His Arg
65                  70                  75                  80

GTG GTG AAG CTG CTG CTG CGC TCC TCC AAC CTG TCC GGG ATC ATC TCG       288
Val Val Lys Leu Leu Leu Arg Ser Ser Asn Leu Ser Gly Ile Ile Ser
                85                  90                  95

CCG TCG CTC GGC AAC CTG TCC TTC CTC AGG GAG CTG GAC CTC GGC GAC       336
Pro Ser Leu Gly Asn Leu Ser Phe Leu Arg Glu Leu Asp Leu Gly Asp
            100                 105                 110

AAC TAC CTC TCC GGC GAG ATA CCA CCG GAG CTC AGC CGT CTC AGC AGG       384
Asn Tyr Leu Ser Gly Glu Ile Pro Pro Glu Leu Ser Arg Leu Ser Arg
        115                 120                 125

CTT CAG CTG CTG GAG CTG AGC GAT AAC TCC ATC CAA GGG AGC ATC CCC       432
Leu Gln Leu Leu Glu Leu Ser Asp Asn Ser Ile Gln Gly Ser Ile Pro
    130                 135                 140

GCG GCC ATT GGA GCA TGC ACC AAG TTG ACA TCG CTA GAC CTC AGC CAC       480
Ala Ala Ile Gly Ala Cys Thr Lys Leu Thr Ser Leu Asp Leu Ser His
145                 150                 155                 160

AAC CAA CTG CGA GGT ATG ATC CCA CGT GAG ATT GGT GCC AGC TTG AAA       528
Asn Gln Leu Arg Gly Met Ile Pro Arg Glu Ile Gly Ala Ser Leu Lys
                165                 170                 175

CAT CTC TCG AAT TTG TAC CTT TAC AAA AAT GGT TTG TCA GGA GAG ATT       576
```

```
                His Leu Ser Asn Leu Tyr Leu Tyr Lys Asn Gly Leu Ser Gly Glu Ile
                                180                 185                 190

CCA TCC GCT TTG GGC AAT CTC ACT AGC CTC CAG GAG TTT GAT TTG AGC           624
Pro Ser Ala Leu Gly Asn Leu Thr Ser Leu Gln Glu Phe Asp Leu Ser
            195                 200                 205

TTC AAC AGA TTA TCA GGA GCT ATA CCT TCA TCA CTG GGG CAG CTC AGC           672
Phe Asn Arg Leu Ser Gly Ala Ile Pro Ser Ser Leu Gly Gln Leu Ser
210                 215                 220

AGT CTA TTG ACT ATG AAT TTG GGA CAG AAC AAT CTA AGT GGG ATG ATC           720
Ser Leu Leu Thr Met Asn Leu Gly Gln Asn Asn Leu Ser Gly Met Ile
225                 230                 235                 240

CCC AAT TCT ATC TGG AAC CTT TCG TCT CTA AGA GCG TTT AGT GTC AGA           768
Pro Asn Ser Ile Trp Asn Leu Ser Ser Leu Arg Ala Phe Ser Val Arg
                245                 250                 255

GAA AAC AAG CTA GGT GGT ATG ATC CCT ACA AAT GCA TTC AAA ACC CTT           816
Glu Asn Lys Leu Gly Gly Met Ile Pro Thr Asn Ala Phe Lys Thr Leu
            260                 265                 270

CAC CTC CTC GAG GTG ATA GAT ATG GGC ACT AAC CGT TTC CAT GGC AAA           864
His Leu Leu Glu Val Ile Asp Met Gly Thr Asn Arg Phe His Gly Lys
        275                 280                 285

ATC CCT GCC TCA GTT GCT AAT GCT TCT CAT TTG ACA GTG ATT CAG ATT           912
Ile Pro Ala Ser Val Ala Asn Ala Ser His Leu Thr Val Ile Gln Ile
    290                 295                 300

TAT GGC AAC TTG TTC AGT GGA ATT ATC ACC TCG GGG TTT GGA AGG TTA           960
Tyr Gly Asn Leu Phe Ser Gly Ile Ile Thr Ser Gly Phe Gly Arg Leu
305                 310                 315                 320

AGA AAT CTC ACA GAA CTG TAT CTC TGG AGA AAT TTG TTT CAA ACT AGA          1008
Arg Asn Leu Thr Glu Leu Tyr Leu Trp Arg Asn Leu Phe Gln Thr Arg
                325                 330                 335

GAA CAA GAT GAT TGG GGG TTC ATT TCT GAC CTA ACA AAT TGC TCC AAA          1056
Glu Gln Asp Asp Trp Gly Phe Ile Ser Asp Leu Thr Asn Cys Ser Lys
            340                 345                 350

TTA CAA ACA TTG AAC TTG GGA GAA AAT AAC CTG GGG GGA GTT CTT CCT          1104
Leu Gln Thr Leu Asn Leu Gly Glu Asn Asn Leu Gly Gly Val Leu Pro
        355                 360                 365

AAT TCG TTT TCC AAT CTT TCC ACT TCG CTT AGT TTT CTT GCA CTT GAA          1152
Asn Ser Phe Ser Asn Leu Ser Thr Ser Leu Ser Phe Leu Ala Leu Glu
    370                 375                 380

TTG AAT AAG ATC ACA GGA AGC ATT CCG AAG GAT ATT GGC AAT CTT ATT          1200
Leu Asn Lys Ile Thr Gly Ser Ile Pro Lys Asp Ile Gly Asn Leu Ile
385                 390                 395                 400

GGC TTA CAA CAT CTC TAT CTC TGC AAC AAC AAT TTC AGA GGG TCT CTT          1248
Gly Leu Gln His Leu Tyr Leu Cys Asn Asn Asn Phe Arg Gly Ser Leu
                405                 410                 415

CCA TCA TCG TTG GGC AGG CTT AAA AAC TTA GGC ATT CTA CTC GCC TAC          1296
Pro Ser Ser Leu Gly Arg Leu Lys Asn Leu Gly Ile Leu Leu Ala Tyr
            420                 425                 430

GAA AAC AAC TTG AGC GGT TCG ATC CCG TTG GCC ATA GGA AAT CTT ACT          1344
Glu Asn Asn Leu Ser Gly Ser Ile Pro Leu Ala Ile Gly Asn Leu Thr
        435                 440                 445

GAA CTT AAT ATC TTA CTG CTC GGC ACC AAC AAA TTC AGT GGT TGG ATA          1392
Glu Leu Asn Ile Leu Leu Leu Gly Thr Asn Lys Phe Ser Gly Trp Ile
    450                 455                 460

CCA TAC ACA CTC TCA AAC CTC ACA AAC TTG TTG TCA TTA GGC CTT TCA          1440
Pro Tyr Thr Leu Ser Asn Leu Thr Asn Leu Leu Ser Leu Gly Leu Ser
465                 470                 475                 480

ACT AAT AAC CTT AGT GGT CCA ATA CCC AGT GAA TTA TTC AAT ATT CAA          1488
Thr Asn Asn Leu Ser Gly Pro Ile Pro Ser Glu Leu Phe Asn Ile Gln
                485                 490                 495

ACA CTA TCA ATA ATG ATC AAT GTA TCA AAA AAT AAC TTG GAG GGA TCA          1536
```

```
         Thr Leu Ser Ile Met Ile Asn Val Ser Lys Asn Asn Leu Glu Gly Ser
                     500                 505                 510

ATA CCA CAA GAA ATA GGG CAT CTC AAA AAT CTA GTA GAA TTT CAT GCA           1584
Ile Pro Gln Glu Ile Gly His Leu Lys Asn Leu Val Glu Phe His Ala
        515                 520                 525

GAA TCG AAT AGA TTA TCA GGT AAA ATC CCT AAC ACG CTT GGT GAT TGC           1632
Glu Ser Asn Arg Leu Ser Gly Lys Ile Pro Asn Thr Leu Gly Asp Cys
530                 535                 540

CAG CTC TTA CGG TAT CTT TAT CTG CAA AAT AAT TTG TTA TCT GGT AGC           1680
Gln Leu Leu Arg Tyr Leu Tyr Leu Gln Asn Asn Leu Leu Ser Gly Ser
545                 550                 555                 560

ATC CCA TCA GCC TTG GGT CAG CTG AAA GGT CTC GAA ACT CTT GAT CTC           1728
Ile Pro Ser Ala Leu Gly Gln Leu Lys Gly Leu Glu Thr Leu Asp Leu
            565                 570                 575

TCA AGC AAC AAT TTG TCA GGC CAG ATA CCC ACA TCC TTA GCA GAT ATT           1776
Ser Ser Asn Asn Leu Ser Gly Gln Ile Pro Thr Ser Leu Ala Asp Ile
            580                 585                 590

ACT ATG CTT CAT TCC TTG AAC CTT TCT TTC AAC AGC TTT GTG GGG GAA           1824
Thr Met Leu His Ser Leu Asn Leu Ser Phe Asn Ser Phe Val Gly Glu
            595                 600                 605

GTG CCA ACC ATT GGT GCT TTC GCA GCT GCA TCC GGG ATC TCA ATC CAA           1872
Val Pro Thr Ile Gly Ala Phe Ala Ala Ala Ser Gly Ile Ser Ile Gln
610                 615                 620

GGC AAT GCC AAA CTC TGT GGT GGA ATA CCT GAT CTA CAT CTG CCT CGA           1920
Gly Asn Ala Lys Leu Cys Gly Gly Ile Pro Asp Leu His Leu Pro Arg
625                 630                 635                 640

TGT TGT CCA TTA CTA GAG AAC AGA AAA CAT TTC CCA GTT CTA CCT ATT           1968
Cys Cys Pro Leu Leu Glu Asn Arg Lys His Phe Pro Val Leu Pro Ile
            645                 650                 655

TCT GTT TCT CTG GCC GCA GCA CTG GCC ATC CTC TCA TCA CTC TAC TTG           2016
Ser Val Ser Leu Ala Ala Ala Leu Ala Ile Leu Ser Ser Leu Tyr Leu
            660                 665                 670

CTT ATA ACC TGG CAC AAG AGA ACT AAA AAG GGA GCC CCT TCA AGA ACT           2064
Leu Ile Thr Trp His Lys Arg Thr Lys Lys Gly Ala Pro Ser Arg Thr
            675                 680                 685

TCC ATG AAA GGC CAC CCA TTG GTC TCT TAT TCG CAG TTG GTA AAA GCA           2112
Ser Met Lys Gly His Pro Leu Val Ser Tyr Ser Gln Leu Val Lys Ala
690                 695                 700

ACA GAT GGT TTC GCG CCG ACC AAT TTG TTG GGT TCT GGA TCA TTT GGC           2160
Thr Asp Gly Phe Ala Pro Thr Asn Leu Leu Gly Ser Gly Ser Phe Gly
705                 710                 715                 720

TCA GTA TAC AAA GGA AAG CTT AAT ATC CAA GAT CAT GTT GCA GTG AAG           2208
Ser Val Tyr Lys Gly Lys Leu Asn Ile Gln Asp His Val Ala Val Lys
            725                 730                 735

GTA CTA AAG CTT GAA AAT CCT AAG GCG CTC AAG AGT TTC ACT GCC GAA           2256
Val Leu Lys Leu Glu Asn Pro Lys Ala Leu Lys Ser Phe Thr Ala Glu
            740                 745                 750

TGT GAA GCA CTA CGA AAT ATG CGA CAT CGA AAT CTT GTC AAG ATA GTT           2304
Cys Glu Ala Leu Arg Asn Met Arg His Arg Asn Leu Val Lys Ile Val
            755                 760                 765

ACA ATT TGC TCG AGC ATT GAT AAC AGA GGG AAC GAT TTC AAA GCA ATT           2352
Thr Ile Cys Ser Ser Ile Asp Asn Arg Gly Asn Asp Phe Lys Ala Ile
            770                 775                 780

GTG TAT GAC TTC ATG CCC AAC GGC AGT CTG GAA GAT TGG ATA CAC CCT           2400
Val Tyr Asp Phe Met Pro Asn Gly Ser Leu Glu Asp Trp Ile His Pro
785                 790                 795                 800

GAA ACA AAT GAT CAA GCA GAC CAG AGG CAC TTG AAT CTG CAT CGA AGA           2448
Glu Thr Asn Asp Gln Ala Asp Gln Arg His Leu Asn Leu His Arg Arg
                805                 810                 815

GTG ACC ATA CTA CTT GAT GTT GCC TGC GCA CTG GAC TAT CTT CAC CGC           2496
```

```
                                                        -continued

Val Thr Ile Leu Leu Asp Val Ala Cys Ala Leu Asp Tyr Leu His Arg
        820                 825                 830

CAT GGC CCT GAA CCT GTT GTA CAC TGT GAT ATT AAA TCA AGC AAT GTG    2544
His Gly Pro Glu Pro Val Val His Cys Asp Ile Lys Ser Ser Asn Val
        835                 840                 845

CTG TTA GAT TCT GAT ATG GTA GCC CAT GTT GGA GAT TTT GGG CTT GCA    2592
Leu Leu Asp Ser Asp Met Val Ala His Val Gly Asp Phe Gly Leu Ala
    850                 855                 860

AGA ATA CTT GTT GAT GGG ACC TCA TTG ATA CAA CAG TCA ACA AGC TCG    2640
Arg Ile Leu Val Asp Gly Thr Ser Leu Ile Gln Gln Ser Thr Ser Ser
865                 870                 875                 880

ATG GGA TTT ATA GGG ACA ATT GGC TAT GCA GCA CCA GGTCAGCAAG         2686
Met Gly Phe Ile Gly Thr Ile Gly Tyr Ala Ala Pro
            885                 890

TCCTTCCAGT ATTTTGCATT TTCTGATCTC TAGTGCTATA TGAAATAGTT TTTACCTCTA  2746

GTGAAACTGA TGGAGAATAT AAGTAATTAA TTGAACTAAT TAAATTGCAC AAAAATAAGA  2806

TTATTTGCCA TATCTATTCA GATGCTAAAT ATAGCTAGTT CATAGAGGTA CAGATTTTTT  2866

TATATAGGAC TCTAGAGCTA CCACACACTC AAATCAAATT ATGGGTGTTT TCTGCTCTAC  2926

ACTGCAATAT GAAATGATTA TTACTTCTAC ATGAACTGAT GGAGGAGTTT CAGAAGGATC  2986

AAATTTGAGT AAATTTTTTC AATTCTACAT TTAAGAAACA CTTTTTTTTC ATATGCTAGT  3046

TACATTTTTT TATTTCACGA GCTTACATTG ACCATGAAAA ATACTTGGCA CTACTTACTA  3106

ATTCCCACAT GGAGGTAGTG AAAATAATAT AGATACAAAA ACGAAATATC CTATGTTGTG  3166

TGATATACTA TAATCACAAT GAACACAAAC AGGATTCGTA CAAAAGTAAT TAGCCATCAT  3226

AGCAACTGAT TGCTTGGGGT AACTGTATAG CACAATCATA CCAAATTTCT TTAGATATGT  3286

ATCTGTAAAT TAGATTCTTA AAGTTAAATA TGAAATTTCA TTGGTATTTA TGTTTCTTTA  3346

TATAATAAAA ATTAATCCAG CCTTTGCATC TATCATTTGT CCAGACATCC TTGTTATTTG  3406

TGATATTTAA CACGTAAATT TACATAATTA TACATCCAAG TTCTTTTTAT TTAACACTGT  3466

AAATTTCAAA TCGTACATGT TATAAAGAAT GTACTATATT TCCTGCTCAA ACA GAG    3522
                                                              Glu

TAT GGC GTT GGG CTC ATT GCA TCA ACG CAT GGA GAT ATT TAC AGC TAT    3570
Tyr Gly Val Gly Leu Ile Ala Ser Thr His Gly Asp Ile Tyr Ser Tyr
        895                 900                 905

GGA ATT CTA GTG CTG GAA ATA GTA ACC GGG AAG CGG CCA ACT GAC AGT    3618
Gly Ile Leu Val Leu Glu Ile Val Thr Gly Lys Arg Pro Thr Asp Ser
910                 915                 920                 925

ACA TTC AGA CCC GAT TTG GGC CTC CGT CAG TAC GTT GAA CTG GGC CTA    3666
Thr Phe Arg Pro Asp Leu Gly Leu Arg Gln Tyr Val Glu Leu Gly Leu
            930                 935                 940

CAT GGC AGA GTG ACG GAT GTT GTT GAC ACG AAG CTC ATT TTG GAT TCT    3714
His Gly Arg Val Thr Asp Val Val Asp Thr Lys Leu Ile Leu Asp Ser
        945                 950                 955

GAG AAC TGG CTG AAC AGT ACA AAT AAT TCT CCA TGT AGA AGA ATC ACT    3762
Glu Asn Trp Leu Asn Ser Thr Asn Asn Ser Pro Cys Arg Arg Ile Thr
        960                 965                 970

GAA TGC ATT GTT TGG CTG CTT AGA CTT GGG TTG TCT TGC TCT CAG GAA    3810
Glu Cys Ile Val Trp Leu Leu Arg Leu Gly Leu Ser Cys Ser Gln Glu
    975                 980                 985

TTG CCA TCG AGT AGA ACG CCA ACC GGA GAT ATC ATC GAC GAA CTG AAT    3858
Leu Pro Ser Ser Arg Thr Pro Thr Gly Asp Ile Ile Asp Glu Leu Asn
990                 995                 1000                1005

GCC ATC AAA CAG AAT CTC TCC GGA TTG TTT CCA GTG TGT GAA GGT GGG    3906
Ala Ile Lys Gln Asn Leu Ser Gly Leu Phe Pro Val Cys Glu Gly Gly
            1010                1015                1020
```

```
            AGC CTT GAA TTC TGA                                                    3921
            Ser Leu Glu Phe
                    1025
```

(2) INFORMATION FOR SEQ ID NO:4:

(i) SEQUENCE CHARACTERISTICS:
        (A) LENGTH: 1025 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ile Ser Leu Pro Leu Leu Phe Val Leu Leu Phe Ser Ala Leu
 1               5                  10                  15

Leu Leu Cys Pro Ser Ser Ser Asp Asp Gly Asp Ala Ala Gly Asp
                20                  25                  30

Glu Leu Ala Leu Leu Ser Phe Lys Ser Ser Leu Leu Tyr Gln Gly Gly
             35                  40                  45

Gln Ser Leu Ala Ser Trp Asn Thr Ser Gly His Gly Gln His Cys Thr
     50                  55                  60

Trp Val Gly Val Val Cys Gly Arg Arg Arg Arg His Pro His Arg
 65                  70                  75                  80

Val Val Lys Leu Leu Leu Arg Ser Ser Asn Leu Ser Gly Ile Ile Ser
                 85                  90                  95

Pro Ser Leu Gly Asn Leu Ser Phe Leu Arg Glu Leu Asp Leu Gly Asp
                100                 105                 110

Asn Tyr Leu Ser Gly Glu Ile Pro Pro Glu Leu Ser Arg Leu Ser Arg
                115                 120                 125

Leu Gln Leu Leu Glu Leu Ser Asp Asn Ser Ile Gln Gly Ser Ile Pro
    130                 135                 140

Ala Ala Ile Gly Ala Cys Thr Lys Leu Thr Ser Leu Asp Leu Ser His
145                 150                 155                 160

Asn Gln Leu Arg Gly Met Ile Pro Arg Glu Ile Gly Ala Ser Leu Lys
                165                 170                 175

His Leu Ser Asn Leu Tyr Leu Tyr Lys Asn Gly Leu Ser Gly Glu Ile
                180                 185                 190

Pro Ser Ala Leu Gly Asn Leu Thr Ser Leu Gln Glu Phe Asp Leu Ser
                195                 200                 205

Phe Asn Arg Leu Ser Gly Ala Ile Pro Ser Ser Leu Gly Gln Leu Ser
    210                 215                 220

Ser Leu Leu Thr Met Asn Leu Gly Gln Asn Asn Leu Ser Gly Met Ile
225                 230                 235                 240

Pro Asn Ser Ile Trp Asn Leu Ser Ser Leu Arg Ala Phe Ser Val Arg
                245                 250                 255

Glu Asn Lys Leu Gly Gly Met Ile Pro Thr Asn Ala Phe Lys Thr Leu
                260                 265                 270

His Leu Leu Glu Val Ile Asp Met Gly Thr Asn Arg Phe His Gly Lys
                275                 280                 285

Ile Pro Ala Ser Val Ala Asn Ala Ser His Leu Thr Val Ile Gln Ile
                290                 295                 300

Tyr Gly Asn Leu Phe Ser Gly Ile Ile Thr Ser Gly Phe Gly Arg Leu
305                 310                 315                 320

Arg Asn Leu Thr Glu Leu Tyr Leu Trp Arg Asn Leu Phe Gln Thr Arg
                325                 330                 335

Glu Gln Asp Asp Trp Gly Phe Ile Ser Asp Leu Thr Asn Cys Ser Lys
```

340                 345                 350
Leu Gln Thr Leu Asn Leu Gly Glu Asn Asn Leu Gly Val Leu Pro
            355                 360                 365

Asn Ser Phe Ser Asn Leu Ser Thr Ser Leu Ser Phe Leu Ala Leu Glu
        370                 375                 380

Leu Asn Lys Ile Thr Gly Ser Ile Pro Lys Asp Ile Gly Asn Leu Ile
385                 390                 395                 400

Gly Leu Gln His Leu Tyr Leu Cys Asn Asn Asn Phe Arg Gly Ser Leu
                405                 410                 415

Pro Ser Ser Leu Gly Arg Leu Lys Asn Leu Gly Ile Leu Leu Ala Tyr
            420                 425                 430

Glu Asn Asn Leu Ser Gly Ser Ile Pro Leu Ala Ile Gly Asn Leu Thr
        435                 440                 445

Glu Leu Asn Ile Leu Leu Leu Gly Thr Asn Lys Phe Ser Gly Trp Ile
450                 455                 460

Pro Tyr Thr Leu Ser Asn Leu Thr Asn Leu Leu Ser Leu Gly Leu Ser
465                 470                 475                 480

Thr Asn Asn Leu Ser Gly Pro Ile Pro Ser Glu Leu Phe Asn Ile Gln
                485                 490                 495

Thr Leu Ser Ile Met Ile Asn Val Ser Lys Asn Asn Leu Glu Gly Ser
            500                 505                 510

Ile Pro Gln Glu Ile Gly His Leu Lys Asn Leu Val Glu Phe His Ala
        515                 520                 525

Glu Ser Asn Arg Leu Ser Gly Lys Ile Pro Asn Thr Leu Gly Asp Cys
    530                 535                 540

Gln Leu Leu Arg Tyr Leu Tyr Leu Gln Asn Asn Leu Leu Ser Gly Ser
545                 550                 555                 560

Ile Pro Ser Ala Leu Gly Gln Leu Lys Gly Leu Glu Thr Leu Asp Leu
                565                 570                 575

Ser Ser Asn Asn Leu Ser Gly Gln Ile Pro Thr Ser Leu Ala Asp Ile
            580                 585                 590

Thr Met Leu His Ser Leu Asn Leu Ser Phe Asn Ser Phe Val Gly Glu
        595                 600                 605

Val Pro Thr Ile Gly Ala Phe Ala Ala Ala Ser Gly Ile Ser Ile Gln
610                 615                 620

Gly Asn Ala Lys Leu Cys Gly Gly Ile Pro Asp Leu His Leu Pro Arg
625                 630                 635                 640

Cys Cys Pro Leu Leu Glu Asn Arg Lys His Phe Pro Val Leu Pro Ile
                645                 650                 655

Ser Val Ser Leu Ala Ala Ala Leu Ala Ile Leu Ser Ser Leu Tyr Leu
            660                 665                 670

Leu Ile Thr Trp His Lys Arg Thr Lys Gly Ala Pro Ser Arg Thr
        675                 680                 685

Ser Met Lys Gly His Pro Leu Val Ser Tyr Ser Gln Leu Val Lys Ala
    690                 695                 700

Thr Asp Gly Phe Ala Pro Thr Asn Leu Leu Gly Ser Gly Ser Phe Gly
705                 710                 715                 720

Ser Val Tyr Lys Gly Lys Leu Asn Ile Gln Asp His Val Ala Val Lys
                725                 730                 735

Val Leu Lys Leu Glu Asn Pro Lys Ala Leu Lys Ser Phe Thr Ala Glu
            740                 745                 750

Cys Glu Ala Leu Arg Asn Met Arg His Arg Asn Leu Val Lys Ile Val
        755                 760                 765

```
Thr Ile Cys Ser Ser Ile Asp Asn Arg Gly Asn Asp Phe Lys Ala Ile
    770                 775                 780
Val Tyr Asp Phe Met Pro Asn Gly Ser Leu Glu Asp Trp Ile His Pro
785                 790                 795                 800
Glu Thr Asn Asp Gln Ala Asp Gln Arg His Leu Asn Leu His Arg Arg
                    805                 810                 815
Val Thr Ile Leu Leu Asp Val Ala Cys Ala Leu Asp Tyr Leu His Arg
                820                 825                 830
His Gly Pro Glu Pro Val Val His Cys Asp Ile Lys Ser Ser Asn Val
            835                 840                 845
Leu Leu Asp Ser Asp Met Val Ala His Val Gly Asp Phe Gly Leu Ala
850                 855                 860
Arg Ile Leu Val Asp Gly Thr Ser Leu Ile Gln Gln Ser Thr Ser Ser
865                 870                 875                 880
Met Gly Phe Ile Gly Thr Ile Gly Tyr Ala Ala Pro Glu Tyr Gly Val
                885                 890                 895
Gly Leu Ile Ala Ser Thr His Gly Asp Ile Tyr Ser Tyr Gly Ile Leu
            900                 905                 910
Val Leu Glu Ile Val Thr Gly Lys Arg Pro Thr Asp Ser Thr Phe Arg
            915                 920                 925
Pro Asp Leu Gly Leu Arg Gln Tyr Val Glu Leu Gly Leu His Gly Arg
930                 935                 940
Val Thr Asp Val Val Asp Thr Lys Leu Ile Leu Asp Ser Glu Asn Trp
945                 950                 955                 960
Leu Asn Ser Thr Asn Asn Ser Pro Cys Arg Arg Ile Thr Glu Cys Ile
                965                 970                 975
Val Trp Leu Leu Arg Leu Gly Leu Ser Cys Ser Gln Glu Leu Pro Ser
            980                 985                 990
Ser Arg Thr Pro Thr Gly Asp Ile Ile Asp Glu Leu Asn Ala Ile Lys
            995                 1000                1005
Gln Asn Leu Ser Gly Leu Phe Pro Val Cys Glu Gly Gly Ser Leu Glu
    1010                1015                1020
Phe
1025

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TCAAGCAACA ATTTGTCAGG NCARATHCC                                      29

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Gly Gln Ile Pro
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TAACAGCACA TTGCTTGATT TNANRTCNCG RTG                                33

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

His Cys Asp Ile Lys
1            5

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(3, 5, 6, 8, 9, 11, 12, 14, 16, 17, 19,
            23)
        (D) OTHER INFORMATION: /product= "OTHER"
            /note= "Xaa = non-conserved amino acid
            residue in rice (Oryza sativa) protein
            RRK-F (Xa21-type disease resistance)
            leucine-rich repeat (LRR)"

(xi) SEQUENCE DESCRIPTION: SEQ ID NO:9:

Pro Ser Xaa Leu Xaa Xaa Leu Xaa Xaa Leu Xaa Xaa Leu Xaa Leu Xaa
1            5                  10                15

Xaa Asn Xaa Leu Ser Gly Xaa Ile
            20

(2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(2, 3, 5, 6, 8, 9, 11, 12, 14, 16, 17, 19,
            21, 22)
        (D) OTHER INFORMATION: /product= "OTHER"
            /note= "Xaa = non-conserved amino acid
            residue in yeast protein adcyc leucine-rich repeat (LRR)"

(xi) SEQUENCE DESCRIPTION: SEQ ID NO:10:

Pro Xaa Xaa Leu Xaa Xaa Leu Xaa Xaa Leu Xaa Xaa Leu Xaa Leu Xaa
1               5                   10                  15

Xaa Asn Xaa Leu Xaa Xaa Leu
            20

(2) INFORMATION FOR SEQ ID NO:11:

(i) SEQUENCE CHARACTERISTICS:
      (A) LENGTH: 24 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: one-of(2, 3, 6, 8, 9, 12, 13, 15, 17, 18, 20,
          22, 23)
      (D) OTHER INFORMATION: /product= "OTHER"
          /note= "Xaa = non-conserved amino acid
          residue in fruit fly (Drosophila)
          protein TO11 leucine-rich repeat (LRR)"

(xi) SEQUENCE DESCRIPTION: SEQ ID NO:11:

Pro Xaa Xaa Leu Phe Xaa His Xaa Xaa Asn Leu Xaa Xaa Leu Xaa Leu
1               5                   10                  15

Xaa Xaa Asn Xaa Leu Xaa Xaa Leu
            20

(2) INFORMATION FOR SEQ ID NO:12:

(i) SEQUENCE CHARACTERISTICS:
      (A) LENGTH: 24 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: one-of(2, 3, 5, 6, 8, 9, 11, 12, 14, 17, 19, 23)
      (D) OTHER INFORMATION: /product= "OTHER"
          /note= "Xaa = non-conserved amino acid
          residue in Arabidopsis protein RLK5
          leucine-rich repeat (LRR)"

(xi) SEQUENCE DESCRIPTION: SEQ ID NO:12:

Pro Xaa Xaa Leu Xaa Xaa Leu Xaa Xaa Leu Xaa Xaa Leu Xaa Leu Ser
1               5                   10                  15

Xaa Asn Xaa Leu Ser Gly Xaa Ile
            20

(2) INFORMATION FOR SEQ ID NO:13:

(i) SEQUENCE CHARACTERISTICS:
      (A) LENGTH: 24 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: one-of(2, 3, 5, 6, 8, 9, 11, 14, 17, 19, 21, 23)
      (D) OTHER INFORMATION: /product= "OTHER"

5,977,434

63

-continued

```
        /note= "Xaa = non-conserved amino acid
        residue in snapdragon protein Fil2
        leucine-rich repeat (LRR)"

(xi) SEQUENCE DESCRIPTION: SEQ ID NO:13:

Pro Xaa Xaa Leu Xaa Xaa Leu Xaa Xaa Leu Xaa Ser Leu Xaa Leu Ser
1               5                  10                  15

Xaa Asn Xaa Leu Xaa Gly Xaa Ile
            20

(2) INFORMATION FOR SEQ ID NO:14:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(2, 3, 4, 5, 6, 8, 9, 11, 12, 14, 17, 19,
            21, 23)
        (D) OTHER INFORMATION: /product= "OTHER"
            /note= "Xaa = non-conserved amino acid
            residue in tomato protein PGIP
            leucine-rich repeat (LRR)"

(xi) SEQUENCE DESCRIPTION: SEQ ID NO:14:

Pro Xaa Xaa Xaa Xaa Xaa Leu Xaa Xaa Leu Xaa Xaa Leu Xaa Leu Ser
1               5                  10                  15

Xaa Asn Xaa Leu Xaa Gly Xaa Ile
            20

(2) INFORMATION FOR SEQ ID NO:15:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(3, 5, 6, 8, 9, 11, 12, 14, 17, 18, 19,
            21, 23)
        (D) OTHER INFORMATION: /product= "OTHER"
            /note= "Xaa = non-conserved amino acid
            residue in tomato protein Cf-9
            leucine-rich repeat (LRR)"

(xi) SEQUENCE DESCRIPTION: SEQ ID NO:15:

Pro Ser Xaa Leu Xaa Xaa Leu Xaa Xaa Leu Xaa Xaa Leu Xaa Leu Ser
1               5                  10                  15

Xaa Xaa Xaa Leu Xaa Gly Xaa Ile
            20

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:
```

```
Ser Trp Asn Thr Ser
1               5
```

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Asp Ile Lys Ser Ser Asn
1               5
```

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Gly Thr Ile Gly Tyr Ala Ala Pro Glu
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = asparagine or glutamine"

(ix) FEATURE:
        (A) NAME/KEY: Modified-site
        (B) LOCATION: 2
        (D) OTHER INFORMATION: /product= "OTHER"
            /note= "Xaa = any amino acid"

(ix) FEATURE:
        (A) NAME/KEY: Modified-site
        (B) LOCATION: 3
        (D) OTHER INFORMATION: /product= "OTHER"
            /note= "Xaa = leucine or valine"

(ix) FEATURE:
        (A) NAME/KEY: Modified-site
        (B) LOCATION: 5
        (D) OTHER INFORMATION: /product= "OTHER"
            /note= "Xaa = glycine or serine"

(ix) FEATURE:
        (A) NAME/KEY: Modified-site
        (B) LOCATION: 6
        (D) OTHER INFORMATION: /product= "OTHER"
            /note= "Xaa = leucine or alanine"

(ix) FEATURE:
        (A) NAME/KEY: Modified-site
        (B) LOCATION: 7

(D) OTHER INFORMATION: /product= "OTHER"
                /note= "Xaa = phenylalanine or valine"

(ix) FEATURE:
             (A) NAME/KEY: Modified-site
             (B) LOCATION: 8
             (D) OTHER INFORMATION: /product= "OTHER"
                 /note= "Xaa = proline or glutamic acid"

(xi) SEQUENCE DESCRIPTION: SEQ ID NO:19:

Xaa Xaa Xaa Ser Xaa Xaa Xaa Xaa
1               5

(2) INFORMATION FOR SEQ ID NO:20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

TAACAGCACA TTGCTTGATT TNANRTCRCA RTG                                     33

(2) INFORMATION FOR SEQ ID NO:21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

TAACAGCACA TTGCTTGATT TNANRTCYCT RTG                                     33

(2) INFORMATION FOR SEQ ID NO:22:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:22:

TAAGCAACAA TTTG                                                          14

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

TAACAGCACA TTGCTTGA                                                      18

(2) INFORMATION FOR SEQ ID NO:24:

(i) SEQUENCE CHARACTERISTICS:
            (A) LENGTH: 1554 base pairs
            (B) TYPE: nucleic acid (C) STRANDEDNESS: single
                (D) TOPOLOGY: linear (ii) MOLECULE TYPE: cDNA (partial)

(xi) SEQUENCE DESCRIPTION: SEQ ID NO:24:

```
TCGACGTCGA ACAATCGCTT GTCTGGTGCA CTTCCTAGTG CTATTGGAAA CTATTCAGGG      60

CTGAAGAATC TTGTGTTAAC TGGAAATGGT TTCTCAGGTG ATATCCCTTC TGATATTGGC     120

AGACTAAAGA GCATCTTAAA GCTGGACCTG AGTAGAAACA ACTTCTCTGG CACAATCCCT     180

CCTCAGATTG GTAACTGTCT TTCCTTAACT TACTTGGATT TGAGCCAAAA TCAACTTTCT     240

GGTCCTATCC CAGTTCAAAT TGCTCAAATT CACATCTTAA ATTACATCAA TATTTCCTGG     300

AATCACTTCA ACGAGAGCCT TCCCGCGGAG ATTGGCTTGA TGAAGAGTTT AACTTCAGCA     360

GATTTTTCCC ACAATAACTT ATCTGGATCA ATACCTGAAA CAGGCCAATA TTTATATTTC     420

AACTCAACTT CCTTCACCGG CAACCCTTAT CTCTCTGGAT CCGACTCGAC TCCTAGCAAC     480

ATTACATCCA ACTCACCGTC AGAACTTGGA GACGGAAGTG ACAGCAGAAC TAAGGTTCCT     540

ACAATATACA AGTTCATATT TGCATTTGGG CTCTTATTCT GCTCCCTCAT TTTCGTTGTC     600

TTAGCAATAA TCAAGACAAG AAAGGGGAGT AAGAATTCAA ATTTGTGGAA GCTGACAGCA     660

TTTCAGAAGC TTGAGTTCGG AAGTGAAGAC GTCTTGCAGT GCTTGAAAGA CAACAACGTC     720

ATAGGGAGAG GTGGAGCAGG GATAGTGTAT AAGGGAACTA TGCCAAATGG TGATCATGTC     780

GCGGTGAAGA AATTGGGAAT AAGCAAAGGC TCACATGATA ACGGCCTATC TGCTGAACTT     840

AACACATTAG GAAGATCAG GCATAGGTAC ATTGTGAGAC TGCTCGCGTT TGTTCAAAC      900

AAGGAAGTCA ACTTGCTAGT TTATGAGTAC ATGCTAAATG GAAGCTTAGG TGAAGTGCTT     960

CATGGGAAGA ACGGCGGGCA ACTCCAATGG GAAACTAGGC TAAAAATAGC CATAGAAGCT    1020

GCCAAGGGCC TTTCTTATTT GCACCACGAT TGCTCCCCTA TGATAATCCA CCGCGATGTC    1080

AAGTCCAACA ATATATTGTT GAACTCTGAA CTTGAAGCTC ATGTTGCAGA TTTTGGATTA    1140

GCCAAGTACT TTCGTAACAA TGGTACCTCT GAGTGCATGT CTGCAATTGC AGGATCTTAT    1200

GGCTACATTG CTCCAGAATA TGCATACACG CTGAAAATTG ATGAGAAAAG CGATGTGTAT    1260

AGCTTTGGAG TGGTGTTGTT GGAGCTTATA ACAGGACGAA GGCCAGTAGG AAATTTTGGA    1320

GAAGAAGGAA TGGACATTGT ACAATGGGCG AAAACGGAGA CAAAATGGAG CAAAGAAGGG    1380

GTGGTGAAAA TCTTGGATGA GAGGCTAAAA AATGTTGCAA TTGTTGAAGC TATGCAAGTA    1440

TTTTTTGTAG CAATGCTTTG TGTTGAAGAG TACAGCATTG AGAGGCCTAC AATGAGGGAA    1500

GTAGTCCAAA TGCTTTCTCA AGCTAAACAA CCAAATACTT TCCAAATCCA ATAA          1554
```

(2) INFORMATION FOR SEQ ID NO:25:

(i) SEQUENCE CHARACTERISTICS:
            (A) LENGTH: 544 amino acids
            (B) TYPE: amino acid
            (C) STRANDEDNESS:
            (D) TOPOLOGY: linear (ii) MOLECULE TYPE: protein (ix) FEATURE:
            (A) NAME/KEY: Protein
            (B) LOCATION: 1..544
            (D) OTHER INFORMATION: /note= "Tomato Receptor Kinase 1 (TRK1)"

(xi) SEQUENCE DESCRIPTION: SEQ ID NO:25:

```
Ser Thr Ser Asn Asn Arg Leu Ser Gly Ala Leu Pro Ser Ala Ile Gly
1               5                   10                  15
```

```
Asn Tyr Ser Gly Leu Lys Asn Leu Val Leu Thr Gly Asn Gly Phe Ser
             20                  25                  30

Gly Asp Ile Pro Ser Asp Ile Gly Arg Leu Lys Ser Ile Leu Lys Leu
         35                  40                  45

Asp Leu Ser Arg Asn Asn Phe Ser Gly Thr Ile Pro Pro Gln Ile Gly
 50                      55                  60

Asn Cys Leu Ser Leu Thr Tyr Leu Asp Leu Ser Gln Asn Gln Leu Ser
 65                  70                  75                  80

Gly Pro Ile Pro Val Gln Ile Ala Gln Ile His Ile Leu Asn Tyr Ile
                 85                  90                  95

Asn Ile Ser Trp Asn His Phe Asn Glu Ser Leu Pro Ala Glu Ile Gly
             100                 105                 110

Leu Met Lys Ser Leu Thr Ser Ala Asp Phe Ser His Asn Asn Leu Ser
             115                 120                 125

Gly Ser Ile Pro Glu Thr Gly Gln Tyr Leu Tyr Phe Asn Ser Thr Ser
 130                 135                 140

Phe Thr Gly Asn Pro Tyr Leu Ser Gly Ser Asp Ser Thr Pro Ser Asn
145                 150                 155                 160

Ile Thr Ser Asn Ser Pro Ser Glu Leu Gly Asp Gly Ser Asp Ser Arg
                 165                 170                 175

Thr Lys Val Pro Thr Ile Tyr Lys Phe Ile Phe Ala Phe Gly Leu Leu
             180                 185                 190

Phe Cys Ser Leu Ile Phe Val Val Leu Ala Ile Ile Lys Thr Arg Lys
             195                 200                 205

Gly Ser Lys Asn Ser Asn Leu Trp Lys Leu Thr Ala Phe Gln Lys Leu
 210                 215                 220

Glu Phe Gly Ser Glu Asp Val Leu Gln Cys Leu Lys Asp Asn Asn Val
225                 230                 235                 240

Ile Gly Arg Gly Gly Ala Gly Ile Val Tyr Lys Gly Thr Met Pro Asn
                 245                 250                 255

Gly Asp His Val Ala Arg Ser Ala Gly Phe Ala Ala Ser Ser Arg
             260                 265                 270

Gly Gly Ile Val Tyr Lys Gly Thr Met Pro Asn Gly Asp His Val Ala
             275                 280                 285

Val Lys Lys Leu Gly Ile Ser Lys Gly Ser His Asp Asn Gly Leu Ser
 290                 295                 300

Ala Glu Leu Asn Thr Leu Gly Lys Ile Arg His Arg Tyr Ile Val Arg
305                 310                 315                 320

Leu Leu Ala Phe Cys Ser Asn Lys Glu Val Asn Leu Leu Val Tyr Glu
             325                 330                 335

Tyr Met Leu Asn Gly Ser Leu Gly Glu Val Leu His Gly Lys Asn Gly
             340                 345                 350

Gly Gln Leu Gln Trp Glu Thr Arg Leu Lys Ile Ala Ile Glu Ala Ala
             355                 360                 365

Lys Gly Leu Ser Tyr Leu His His Asp Cys Ser Pro Met Ile Ile His
 370                 375                 380

Arg Asp Val Lys Ser Asn Asn Ile Leu Leu Asn Ser Glu Leu Glu Ala
385                 390                 395                 400

His Val Ala Asp Phe Gly Leu Ala Lys Tyr Phe Arg Asn Asn Gly Thr
                 405                 410                 415

Ser Glu Cys Met Ser Ala Ile Ala Gly Ser Tyr Gly Tyr Ile Ala Pro
             420                 425                 430

Glu Tyr Ala Tyr Thr Leu Lys Ile Asp Glu Lys Ser Asp Val Tyr Ser
             435                 440                 445
```

```
Phe Gly Val Val Leu Leu Glu Leu Ile Thr Gly Arg Arg Pro Val Gly
    450                 455                 460

Asn Phe Gly Glu Glu Gly Met Asp Ile Val Gln Trp Ala Lys Thr Glu
465                 470                 475                 480

Thr Lys Trp Ser Lys Glu Gly Val Val Lys Ile Leu Asp Glu Arg Leu
                485                 490                 495

Lys Asn Val Ala Ile Val Glu Ala Met Gln Val Phe Phe Val Ala Met
                500                 505                 510

Leu Cys Val Glu Glu Tyr Ser Ile Glu Arg Pro Thr Met Arg Glu Val
            515                 520                 525

Val Gln Met Leu Ser Gln Ala Lys Gln Pro Asn Thr Phe Gln Ile Gln
    530                 535                 540
```

(2) INFORMATION FOR SEQ ID NO:26:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (partial)

(ix) FEATURE:
        (A) NAME/KEY: CDS
        (B) LOCATION: 1..495
        (D) OTHER INFORMATION: /product= "Tomato Receptor Like 1
        (TRL1)"

(ix) FEATURE:
        (A) NAME/KEY: unsure
        (B) LOCATION: replace(15, "G")
        (D) OTHER INFORMATION: /note= "Nucleotide at position 15 can be
            either A or G (R)"

(xi) SEQUENCE DESCRIPTION: SEQ ID NO:26:

```
TCA AGC AAC AAT TTA TCA GGA CAA ATA CCT TCA GGC TTG GCC AAT GTG        48
Ser Ser Asn Asn Leu Ser Gly Gln Ile Pro Ser Gly Leu Ala Asn Val
 1               5                  10                  15

ACC ACA CTG GCA GCA TTT AAC GTT TCT TTC AAT AAT CTG TCT GGG CCA        96
Thr Thr Leu Ala Ala Phe Asn Val Ser Phe Asn Asn Leu Ser Gly Pro
                20                  25                  30

CTG CCT CTT AAC AAA GAT TTG ATG AAG TGT AAT AGT GTT CAG GGA AAC       144
Leu Pro Leu Asn Lys Asp Leu Met Lys Cys Asn Ser Val Gln Gly Asn
            35                  40                  45

CCC TTT CTG CAA TCG TGC CAT GTA TTT TCT CTA TCA ACA CCT TCT ACA       192
Pro Phe Leu Gln Ser Cys His Val Phe Ser Leu Ser Thr Pro Ser Thr
        50                  55                  60

GAT CAG CAG GGA AGA ATA GGG GAC TCA CAA GAT TCT GCT GCG TCT CCT       240
Asp Gln Gln Gly Arg Ile Gly Asp Ser Gln Asp Ser Ala Ala Ser Pro
65                  70                  75                  80

TCA GGT TCA ACC CAG AAA GGA GGG TGC AGC GGT TTC AAC TCC ATA GAG       288
Ser Gly Ser Thr Gln Lys Gly Gly Cys Ser Gly Phe Asn Ser Ile Glu
                85                  90                  95

ATT GCA TCC ATA ACA TCT GCG GCA GCT ATT GTG TCA GTT CTT CTT GCT       336
Ile Ala Ser Ile Thr Ser Ala Ala Ala Ile Val Ser Val Leu Leu Ala
            100                 105                 110

CTG ATA GTC CTG TTC TTT TAC ACC AGA AAA TGG AAT CCA AGA TCT AGA       384
Leu Ile Val Leu Phe Phe Tyr Thr Arg Lys Trp Asn Pro Arg Ser Arg
        115                 120                 125

GTT GCT GGA TCT ACC AGG AAA GAA GTC ACA GTG TTT ACA GAA GTT CCG       432
Val Ala Gly Ser Thr Arg Lys Glu Val Thr Val Phe Thr Glu Val Pro
130                 135                 140
```

-continued

```
GTT CCT TTA ACA TTT GAA AAT GTA GTG CGG GCC ACA GAG ATC TCA AAT         480
Val Pro Leu Thr Phe Glu Asn Val Val Arg Ala Thr Glu Ile Ser Asn
145                 150                 155                 160

CAA GCA ATG TGC TGT T                                                   496
Gln Ala Met Cys Cys
                165
```

(2) INFORMATION FOR SEQ ID NO:27:

(i) SEQUENCE CHARACTERISTICS:
      (A) LENGTH: 165 amino acids
      (B) TYPE: amino acid
      (D) TOPOLOGY: linear (ii) MOLECULE TYPE: protein (xi) SEQUENCE DESCRIPTION: SEQ ID NO:27:

```
Ser Ser Asn Asn Leu Ser Gly Gln Ile Pro Ser Gly Leu Ala Asn Val
1               5                   10                  15

Thr Thr Leu Ala Ala Phe Asn Val Ser Phe Asn Asn Leu Ser Gly Pro
                20                  25                  30

Leu Pro Leu Asn Lys Asp Leu Met Lys Cys Asn Ser Val Gln Gly Asn
            35                  40                  45

Pro Phe Leu Gln Ser Cys His Val Phe Ser Leu Ser Thr Pro Ser Thr
        50                  55                  60

Asp Gln Gln Gly Arg Ile Gly Asp Ser Gln Asp Ser Ala Ala Ser Pro
65                  70                  75                  80

Ser Gly Ser Thr Gln Lys Gly Gly Cys Ser Gly Phe Asn Ser Ile Glu
                85                  90                  95

Ile Ala Ser Ile Thr Ser Ala Ala Ala Ile Val Ser Val Leu Leu Ala
                100                 105                 110

Leu Ile Val Leu Phe Phe Tyr Thr Arg Lys Trp Asn Pro Arg Ser Arg
            115                 120                 125

Val Ala Gly Ser Thr Arg Lys Glu Val Thr Val Phe Thr Glu Val Pro
            130                 135                 140

Val Pro Leu Thr Phe Glu Asn Val Val Arg Ala Thr Glu Ile Ser Asn
145                 150                 155                 160

Gln Ala Met Cys Cys
                165
```

PROCEDURES AND MATERIALS FOR CONFERRING DISEASE RESISTANCE IN PLANTS

This is a continuation in part of copending U.S. patent application Ser. No. 08/567,375, filed Dec. 4, 1995, which is a continuation in part of U.S. provisional patent application No., 60/004,645, filed Sep. 24, 1995. It is also a continuation in part of U.S. patent application Ser. No. 08/475,891, filed Jun. 7, 1995, now U.S. Pat. No. 5,859,339, which is a continuation in part of U.S. patent application No. Ser. 08/373,375, filed Jan. 17, 1995, abandoned. These applications are incorporated herein by reference.

STATEMENT AS TO RIGHTS TO INVENTIONS MADE UNDER FEDERALLY SPONSORED RESEARCH AND DEVELOPMENT

This invention was made with Government support under Grant No. GM47907, awarded by the National Institutes of Health and Grant No. 9300834, awarded by the United States Department of Agriculture. The Government has certain rights in this invention.

FIELD OF THE INVENTION

The present invention relates generally to plant molecular biology. In particular, it relates to nucleic acids and methods for conferring disease resistance in plants.

BACKGROUND OF THE INVENTION

Loci conferring disease resistance have been identified in many plant species. Genetic analysis of many plant-pathogen interactions has demonstrated that plants contain loci that confer resistance against specific races of a pathogen containing a complementary avirulence gene. Molecular characterization of these genes should provide means for conferring disease resistance to a wide variety of crop plants.

Those plant resistance genes that have been characterized at the molecular level fall into four classes. One gene, Hm1 in corn, encodes a reductase and is effective against the fungal pathogen *Cochliobolus carbonum* (Johal et al. *Science* 258:985–987 (1992)). In tomato, the Pto gene confers resistance against *Pseudomonas syringae* that express the avrPto avirulence gene (Martin et al. *Science* 262:1432 (1993)). The predicted Pto gene encodes a serine threonine protein kinase. The tomato Cf-9 gene confers resistance to races of the fungus *Cladosporium fulvum* that carry the avirulence gene Avr9 (Jones et al. *Science* 266:789–793 (1994). The tomato Cf-9 gene encodes a putative extracellular LRR protein. Finally, the RPS2 gene of *Arabidopsis thaliana* confers resistance to *P. syringae* that express the avrRpt2 avirulence gene (Bent et al. *Science* 265:1856–1860 (1994)). RPs2 encodes a protein with an LRR motif and a P-loop motif.

Bacterial blight disease caused by Xanthomonas spp. infects virtually all crop plants and leads to extensive crop losses worldwide. Bacterial blight disease of rice (*Oryza sativa*), caused by *Xanthomonas oryzae* pv. *oryzae* (Xoo), is an important disease of this crop. Races of Xoo that induce resistant or susceptible reactions on rice cultivars with distinct resistance (Xa) genes have been identified. One source of resistance (Xa21) had been identified in the wild species *Oryza longistaminata* (Khush et al. in *Proceedings of the International Workshop on Bacterial Blight of Rice.* (International Rice Research Institute, 1989) and Ikeda et al. *Jpn J. Breed* 40 (Suppl. 1):280–281 (1990)). Xa21 is a dominant resistance locus that confers resistance to all known isolates of Xoo and is the only characterized Xa gene that carries resistance to Xoo race 6. Genetic and physical analysis of the Xa21 locus has identified a number of tightly linked markers on chromosome 11 (Ronald et al. *Mol. Gen. Genet.* 236:113–120 (1992)). The molecular mechanisms by which the Xa21 locus confers resistance to this pathogen were not identified, however.

Considerable effort has been directed toward cloning plant genes conferring resistance to a variety of bacterial, fungal and viral diseases. Only one pest resistance gene has been cloned in monocots. Since monocot crops feed most humans and animals in the world, the identification of disease resistance genes in these plants is particularly important. The present invention addresses these and other needs.

SUMMARY OF THE INVENTION

The present invention provides isolated nucleic acid constructs comprising an RRK polynucleotide sequence, which hybridizes to SEQ ID NO:1 or to SEQ ID NO:3 under stringent conditions. Exemplary RRK polynucleotide sequences are Xa21 sequences which encode an Xa21 polypeptide as shown in SEQ ID NO:4. The RRK polynucleotides encode a protein having a leucine rich repeat motif and/or a cytoplasmic protein kinase domain. The nucleic acid constructs of the invention may further comprise a promoter operably linked to the RRK polynucleotide sequence. The promoter may be a tissue-specific promoter or a constitutive promoter.

The invention also provides nucleic acid constructs comprising a promoter sequence from an RRK gene linked to a heterologous polynucleotide sequence. Exemplary heterologous polynucleotide sequences include structural genes which confer pathogen resistance on plants.

The invention further provides transgenic plants comprising a recombinant expression cassette comprising a promoter from an RRK gene operably linked to a polynucleotide sequence as well as transgenic plants comprising a recombinant expression cassette comprising a plant promoter operably linked to an RRK polynucleotide sequence. Although any plant can be used in the invention, rice and tomato plants may be conveniently used.

The invention further provides methods of enhancing resistance to Xanthomonas in a plant. The methods comprise introducing into the plant a recombinant expression cassette comprising a plant promoter operably linked to an RRK polynucleotide sequence. The methods may be conveniently carried out with rice or tomato plants.

Definitions

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

A "heterologous sequence" is one that originates from a foreign species, or, if from the same species, is substantially modified from its original form. For example, a promoter operably linked to a heterologous structural gene is from a species different from that from which the structural gene was derived, or, if from the same species, one or both are substantially modified from their original form.

An "RRK gene" is member of a new class of disease resistance genes which encode RRK polypeptides comprising an extracellular LRR domain, a transmembrane domain, and a cytoplasmic protein kinase domain (as shown in e.g., RLK5, Pto and Fen (Martin et al. *Plant Cell* 6:1543–1552 (1994)). As used herein, an LRR domain is a region of a repeated unit of about 24 residues as shown in FIG. 1 and found in Cf-9 and RLK5). Using the sequences disclosed here and standard nucleic acid hybridization and/or amplification techniques, one of skill can identify members of this class of genes. For instance, a nucleic acid probe from an Xa21 gene detected polymorphisms that segregated with the blast (*Pyricularia oryzae*) resistance gene (Pi7) in 58 recombinant inbred lines of rice. The same probe also detected polymorphism in nearly isogenic lines carrying xa5 and Xa10 resistance genes.

In some preferred embodiments, members of this class of disease resistance genes can be identified by their ability to be amplified by degenerate PCR primers which correspond to the LRR and kinase domains. For instance, primers have been used to isolate homologous genes in tomato. Exemplary primers for this purpose are tcaagcaacaatttgtcaggnca a/g at a/c/t cc (SEQ ID NO:5) (for the LRR domain sequence GQIP (SEQ ID NO:6)) and taacagcacattgcttgatttnan g/a tcncg g/a tg (SEQ ID NO:7) (the kinase domain sequence HCDIK (SEQ ID NO:8)).

An "Xa21 polynucleotide sequence" is a subsequence or full length polynucleotide sequence of an Xa21 gene, such as the rice Xa21 gene, which, when present in a transgenic plant confers resistance to Xanthomonas spp. (e.g., *X. oryzae*) on the plant. Exemplary polynucleotides of the invention include the coding region of SEQ ID NO:3. An Xa21 polynucleotide is typically at least about 3100 nucleotides to about 6500 nucleotides in length, usually from about 4000 to about 4500 nucleotides.

An "Xa21 polypeptide" is a gene product of an Xa21 polynucleotide sequence, which has the activity of Xa21, i.e., the ability to confer resistance to Xanthomonas spp. Xa21 polypeptides, like other RRK polypeptides, are characterized by the presence of an extracellular domain comprising a region of leucine rich repeats (LRR) and/or a cytoplasmic protein kinase domain. Exemplary Xa21 polypeptides of the invention include SEQ ID NO:4.

In the expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional RRK polypeptide, one of skill will recognize that because of codon degeneracy, a number of polynucleotide sequences will encode the same polypeptide. These variants are specifically covered by the term "RRK polynucleotide sequence". In addition, the term specifically includes those full length sequences substantially identical (determined as described below) with an RRK gene sequence and that encode proteins that retain the function of the RRK protein. Thus, in the case of rice RRK genes disclosed here, the above term includes variant polynucleotide sequences which have substantial identity with the sequences disclosed here and which encode proteins capable of conferring resistance to Xanthomonas or other plant diseases and pests on a transgenic plant comprising the sequence.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segment or "comparison window" to identify and compare local regions of sequence similarity. The segment used for purposes of comparison may be at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under appropriate conditions. Appropriate conditions can be high or low stringency and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. For Southern hybridizations, high stringency wash conditions will include at least one wash in 0.1× SSC at 65° C.

Nucleic acids of the invention can be identified from a cDNA or genomic library prepared according to standard procedures and the nucleic acids disclosed here (e.g., SEQ ID NO:1 or 3) used as a probe. Low stringency hybridization conditions will typically include at least one wash using 2× SSC at 65° C. The washes are preferably followed by a subsequent wash using 1× SSC at 65° C.

As used herein, a homolog of a particular RRK gene (e.g., the rice Xa21 gene disclosed here) is a second gene (either in the same species or in a different species) which encodes a protein having an amino acid sequence having at least 25% identity or 45% similarity to (determined as described above) to a polypeptide sequence in the first gene product. It is believed that, in general, homologs share a common evolutionary past.

BRIEF DESCRIPTION OF THE DRAWINGS

FIG. 1 shows a comparison of leucine rich repeat proteins (RICE, SEQ ID NO:9; yeast, SEQ ID NO:10; fly, SEQ ID NO:11; arab, SEQ ID NO:12; snap, SEQ ID NO:13; tomato PGIP, SEQ ID NO:14; tomato CF9, SEQ ID NO:15).

DESCRIPTION OF THE PREFERRED EMBODIMENTS

Figure 2A:
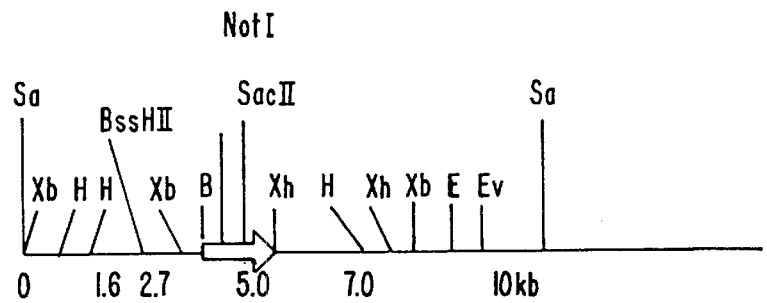
FIGS. 2A–F show partial restriction maps of BAC and cosmid clones containing regions that hybridized to Xa21-specific probes.
Figure 2B:
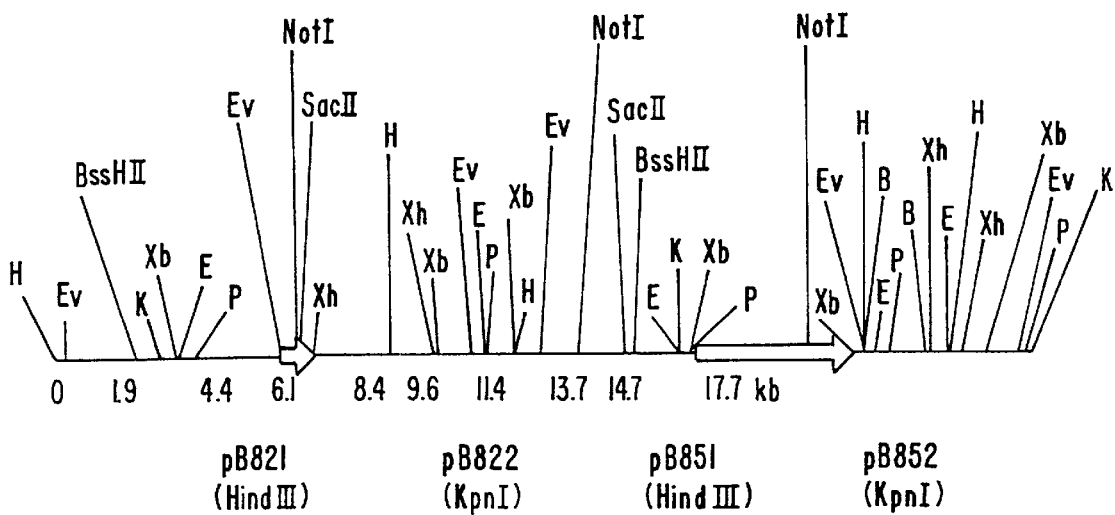
Figure 2C:
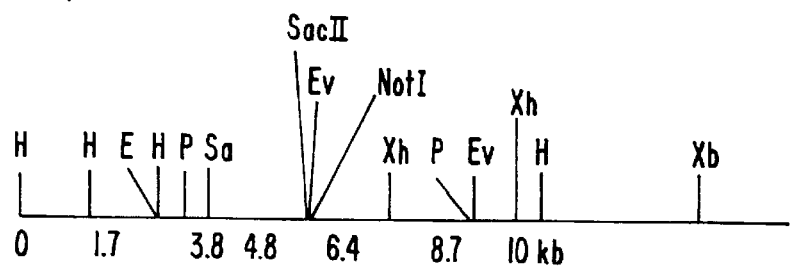
Figure 2D:
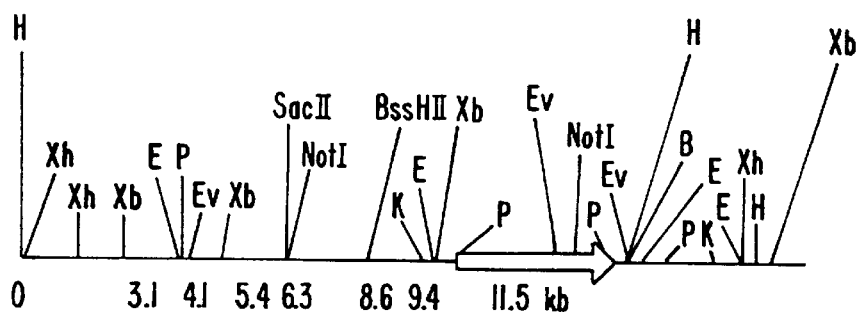
Figure 2E:
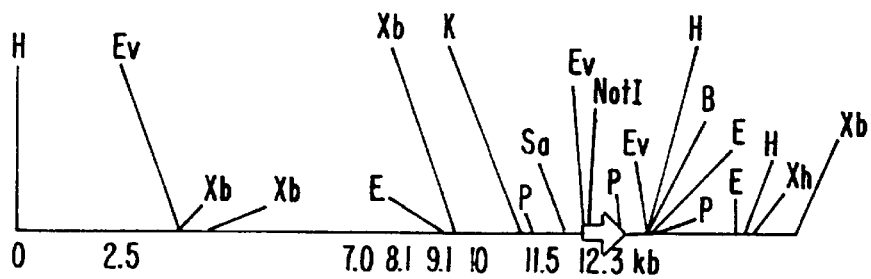

This invention relates to plant RRK genes, such as the Xa21 genes of rice. Nucleic acid sequences from RRK genes, in particular Xa21 genes, can be used to confer resistance to Xanthomonas and other pathogens in plants. The invention has use in conferring resistance in all higher plants susceptible to pathogen infection. The invention thus has use over a broad range of types of plants, including species from the genera Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Zea, Avena, Hordeum, Secale, Triticum, and, Sorghum.

The Example section below, which describes the isolation and characterization of Xa21 genes in rice, is exemplary of a general approach for isolating Xa21 genes and other RRK genes. The isolated genes can then be used to construct recombinant vectors for transferring RRK gene expression to transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

The isolation of Xa21 and related RRK genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaf and a cDNA library which contains the RRK gene transcript is prepared from the mRNA. Alternatively, cDNA may be prepared from mRNA extracted from other tissues in which RRK genes or homologs are expressed.

The cDNA or genomic library can then be screened using a probe based upon the sequence of a cloned RRK gene such as rice Xa21 genes disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the RRK and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying RRK sequences from plant tissues are generated from comparisons of the sequences provided herein. For a general overview of PCR see *PCR Protocols: A Guide to Methods and Applications.* (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Isolated sequences prepared as described herein can then be used to provide RRK gene expression and therefore Xanthomonas resistance in desired plants. One of skill will recognize that the nucleic acid encoding a functional RRK protein (e.g., SEQ ID NO:2 and 4) need not have a sequence identical to the exemplified gene disclosed here. In addition, the polypeptides encoded by the RRK genes, like other proteins, have different domains which perform different functions. Thus, the RRK gene sequences need not be full length, so long as the desired functional domain of the protein is expressed. As explained in detail below, the proteins of the invention comprise an extracellular leucine rich repeat domain, as well as an intracellular kinase domain. Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other pest resistance genes. For example, the extra cellular domain (including the leucine rich repeat region) of the proteins of the invention can be replaced by that of the tomato Cf-9 gene and thus provide resistance to fungal pathogens of rice. These modifications can be used in a number of combinations to produce the final modified protein chain.

To use isolated RRK sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988).

A DNA sequence coding for the desired RRK polypeptide, for example a cDNA or a genomic sequence encoding a full length protein, will be used to construct a recombinant expression cassette which can be introduced into the desired plant. An expression cassette will typically comprise the RRK polynucleotide operably linked to transcriptional and translational initiation regulatory sequences which will direct the transcription of the sequence from the RRK gene in the intended tissues of the transformed plant.

For example, a plant promoter fragment may be employed which will direct expression of the RRK in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens,* and other transcription initiation regions from various plant genes known to those of skill.

Alternatively, the plant promoter may direct expression of the RRK gene in a specific tissue or may be otherwise under more precise environmental or developmental control. Such promoters are referred to here as "inducible" promoters. Examples of environmental conditions that may effect transcription by inducible promoters include pathogen attack, anaerobic conditions, or the presence of light.

Examples of promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations.

The endogenous promoters from the RRK genes of the invention can be used to direct expression of the genes. These promoters can also be used to direct expression of heterologous structural genes. Thus, the promoters can be used in recombinant expression cassettes to drive expression of genes conferring resistance to any number of pathogens, including fungi, bacteria, and the like.

To identify the promoters, the 5' portions of the clones described here are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. J. Messing et al., in *Genetic Engineering in Plants,* pp. 221–227 (Kosage, Meredith and Hollaender, eds. 1983).

If proper polypeptide expression is desired, a polyadenylation region at the 3'-end of the RRK coding region should be included. The polyadenylation region can be derived from the natural gene, from a variety of other plant genes, or from T-DNA.

The vector comprising the sequences from an RRK gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Transformation techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987). Using a number of approaches, cereal species such as rye (de la Pena et al., *Nature* 325:274–276 (1987)), corn (Rhodes et al., *Science* 240:204–207 (1988)), and rice (Shimamoto et al., *Nature* 338:274–276 (1989) by electroporation; Li et al. *Plant Cell Rep.* 12:250–255 (1993) by ballistic techniques) can be transformed.

*Agrobacterium tumefaciens*-meditated transformation techniques are well described in the scientific literature. See, for example Horsch et al. *Science* 233:496–498 (1984), and Fraley et al. *Proc. Natl. Acad. Sci. USA* 80:4803 (1983). Although Agrobacterium is useful primarily in dicots, certain monocots can be transformed by Agrobacterium. For instance, Agrobacterium transformation of rice is described by Hiei et al, *Plant J.* 6:271–282 (1994).

Transformed plant cells which are derived by any of the above transformation techniques can be cultured to regenerate a whole plant which possesses the transformed genotype and thus the desired RRK-controlled phenotype. Such regeneration techniques rely on manipulation of certain phytohormones in a tissue culture growth medium, typically relying on a biocide and/or herbicide marker which has been introduced together with the RRK nucleotide sequences. Plant regeneration from cultured protoplasts is described in Evans et al., *Protoplasts Isolation and Culture, Handbook of Plant Cell Culture*, pp. 124–176, MacMillan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the RRK polynucleotides into transformed plants in ways and under circumstances which are not found naturally. In particular, the RRK polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of RRK gene expression can be measured by detection of increases or decreases in mRNA levels using, for instance, Northern blots. In addition, the phenotypic effects of gene expression can be detected by measuring lesion length as in plants. Suitable assays for determining resistance are described below.

The following Examples are offered by way of illustration, not limitation.

EXAMPLE 1

Plant genes may also be isolated using map-based cloning methods. This strategy consists of identifying DNA markers that are tightly linked to the gene or genes of interest. One requirement for the success of map-based cloning and physical analysis of large chromosomal regions is the availability of libraries containing large inserts of genomic DNA. Recently, Shizuya, H., et al., *Proc. Natl. Acad. Sci.* 89, 8794–8797 (1992), described a bacterial artificial chromosome (BAC) system to clone large DNA fragments of the human genome. This system utilizes an F-factor-based vector and is capable of maintaining human genomic DNA fragments of >300 kb. DNA can be cloned with high efficiency, manipulated easily and stably maintained in *E. coli*. The following is a description of the use of this technique to isolate genes of the invention.

Isolation of BAC and Cosmid Clones Carrying
Xa21-related Sequences BAC Clones

A. Materials and Methods

Preparation of high molecular weight DNA in rice

An International Rice Research Institute (IRRI) rice line, IR-BB21 carrying Xa-21 was used as the plant material. The plants were grown in the greenhouse for 3–5 weeks. Leaf tissue was harvested and washed with distilled water before grinding. High molecular weight DNA was extracted from rice tissue essentially as described by Hatano, S., et al., *Plant Sciences*, 83, 55–64, (1992) and Zhang, H. B., et al., *Plant J.* 7:175–184 (1994), with the following modifications: approximately 20 grams of leaf tissue was ground into powder using a cold mortar and pestle in liquid nitrogen. The powder was suspended by stirring in 200 ml cold nuclei-extraction (NE) buffer (1 MM spermidine, 1 mM spermine, 10 mM $Na_2$ EDTA, 10 mM Trizma base, 80 mM KCl, 0.5% Triton-X 100 and 0.4 M sucrose, pH 9.4). The mixture was filtered through two layers of cheesecloth into a GSA bottle and centrifuged at 1200 g at 4° C. for 20 min. The supernatant was poured off and the nuclear pellet (pale green) was resuspended in 50 ml cold NE Buffer. The resuspended pellet was then filtered through an 80-micron sieve into a 50 ml tube to remove green tissue debris and then centrifuged at 1000 g for 10 min. The pellet was resuspended and centrifuged as above without passing through the 80-micron sieves. The nuclear pellet (about $5 \times 10^8$ nuclei/ml) was resuspended in 2.5 ml of SCE buffer (1M sorbitol, 0.1M NaCitrate, 60 mM EDTA, pH 7.0) and embedded in 2.5 ml 1% low-melting-point (LMP) agarose (Ultrapure). 80 μl plugs were incubated in 25 ml ESP solution (0.5M EDTA, pH 9.3, 1% sodium laurel sarcosine, 5 mg/ml proteinase K, Boehringer Mannheim) at 50° C. for two days with one change of the buffer. Each plug contained about 5 μg DNA.

Partial digestion of high molecular weight DNA and size fraction by PFGE

Agarose plugs were dialyzed twice against TE (10 mM Tris-HCl and 1 mM EDTA, pH 8.0) plus 1 mM PMSF (phenylmethyl sulphonyl fluoride) at 50° C. for one h, and then equilibrated with HindIII buffer (50 mM NaCl, 10 mM Tris-HCl, 10 mM $MgCl_2$ and 1 mM dithiothreitol, pH 7.9)

twice at room temperature for one hr. Plugs were melted at 65° C. for 15 min and kept at 37° C. for 5 min before partial digestion. Five to seven units of HindIII (NEB, USA) per plug were added to the DNA solution and incubated at 37° C. for 30 min. The reaction was stopped by addition of 1/10 volume of 0.5 M EDTA, pH 8.0. Partially digested DNA was immediately loaded into a 0.8% LMP agarose gel with a pipette tip cut off to an inside diameter of 2 mm and separated by PFGE (CHEF DR II system, BioRad, USA). Two different PFGE methods were used for the library construction. Firstly, the gel was subjected to electrophoresis at 150V, using an 8 s initial and 8 s final switch time for 16 h at 14° C. The unresolved DNA ($\geq$200 kb) was focused into a thin band. Secondly, the gel was subject to electrophoresis at 150V, ramped switching time from 60 to 90 s for 16 h at 14° C. For both methods, the gel containing the partially digested DNA was cut and soaked in TE while the marker lanes of the gel were stained with ethidium bromide. The agarose slice containing fragments larger than 200 kb (the first PFGE method) or agarose slice containing 250–350 kb (the second method) was excised from the gel. The agarose slice was equilibrated in TE for 2 h at 4° C., placed in a 1.5 ml tube, melted at 65° C. for 10 min, digested with Gelase (Epicentre, USA) (one unit of enzyme per 100 mg agarose) and incubated at 45° C. for one hr. The DNA solution was directly used for the ligation reaction.

Isolation and preparation of vector, and ligation reaction

The vector, pBeloBAC II, was provided by Drs. H. Shizuya and M. Simon (California Institute of Technology, USA). This vector contains the lacz gene inserted into the vector pBAC108L. Shizuya, et al. (1992). A single colony was inoculated into 5 ml LB media containing 12.5 μg/ml chloramphenicol and grown at 37° C. for 4–5 h before adding to 6 liters of LB media. The inoculum was grown for about 16 h at 37° C. to an OD 1.3–1.5. The plasmid was isolated using Qiagen's plasmid maxi isolation kit (Qiagen, USA). Vector DNA was further purified by cesium chloride/ ethidium bromide equilibrium centrifugation at 45,000 RPM for 60 h. The rotor was decelerated to 35,000 RPM for one hr. to allow the gradient to relax, using a fixed anger rotor 70.1 (Beckman, USA). The plasmid was digested with HindIII to completion and assayed by gel electrophoresis. Vector ends were dephosphorylated with HK phosphatase (Epicenter, USA) at 30° C. for one hr., using 1 unit of the enzyme per 1 μg of vector DNA. The HK phosphatase was inactivated by heating at 65° C. for 30 min. The ligation was carried out in a 100 μl volume in which about 40 ng of the size-selected rice DNA (about 85 μl) was ligated to 10 ng of HindIII-digested vector (1 μl) molar ratio of about 10 to 1 in vector excess) with 400 units of T4 DNA ligase (NEB, USA) at 16° C. overnight. Before transformation, the litigation was dialyzed against TE in an ULTRAFREE-MC filter tube Millipore, USA) at 4° C. overnight.

BAC transformation

Transformation of competent E. coli DH10B cells (GIBCOBRL, USA) was carried out by electroporation using a Cell-Porator (GIBCO-BRL, USA) at the following settings: voltage: 400; charge rate: fast; voltage booster resistance: 4,000; capacitance: 330μ; impedance: low. Thirteen μl of competent cells were mixed with 0.5–1.0 μl of ligation solution for each electroporation. After electroporation, cells were transferred to 1 ml SOC solution (2% Bacto tryptone, 0.5% Bacto yeast extract, 10 MM NaCl, 2.5 mM KCl, 10 mM $MgCl_2$, 10 mM $MgSO_4$, 20 mM Glucose, pH 7.0) and incubated at 37° C. with gentle shaking (90–95 RPM,) for 45 min. The cells were spread on LB plates containing chloramphenicol (12.5 ,g/ml), X-gal (40 ,g/ml) and IPTG (isopropylthio-β-D-galactoside) (0.072 μg/ml). Plates were incubated at 37° C. for 24 h. White colonies containing rice DNA inserts were picked to a new LB plate for a second color screen. The BAC clones were transferred to 384-well microtiter plates (Genetix, UK) containing 60 μl of LB freezing buffer (36 mM $K_2HPO_4$, 13.2 mM $KH_2PO_4$, 1.7 mM Citrate, 0.4 MM $MgSO_4$, 6.8 mM $(NH_4)_2SO_4$, 4.4% v/v Glycerol, 12.5 ,g/ml chloramphenicol, LB) and incubated at 37° C. for 24 h. Since more than 95% of the colonies were still white on the second screen, only one screen was used in the subsequent experiments, and white colonies were directly picked to 384-well microtiter plates. The library was replicated in duplicate and stored in two different –80° C. freezers.

Filter preparation

The BAC clones in each 384-well microtiter plate were replicated onto a Hybond $N^+$ filter (Amersham, USA). The filter was put into a plastic box containing LB/agar with 12.5 μg/ml chloramphenicol and the box was kept at 37° C. overnight until the colonies were about 2–3 mm in diameter. Treatment of the filters was as described. Nizetic, D., et al., Nucl. Acids Res. 19, 182 (1990); Hoheisel, J. D., et al., Cell, 73, 109–120 (1993). Hybridization and washing conditions were the same as described in Hoheisel, et al. (1993). Probes were labeled using random primer extension. Feinberg, A. P. and Vogelstein, B., Anal. Biochem. 132, 6–13 (1983); Addendum 137, 266–267 (1984).

B. Results

The BAC library described above of consists of 11,000 clones. The library was constructed using two different approaches. A first half of the library having 7269 BAC clones was made with one size selection using a compression zone method as described in Ramsay, M. and Wicking, C., Protocols in Human Molecular Genetics, 197–221 (1991). A second half of the library having 3731 clones was made using double size-selection of partially digested DNA. Double size-selection failed, however, to increase the average DNA insert size. Apparently, there were small DNA molecules still present in the size-selected DNA solution (only 250–350 kb DNA isolated). Subsequent experiments demonstrated that double size-selection of DNA between 350–500 kb for ligation yielded larger average insert size in BAC clones. Out of 54 random BAC clones chosen from the library, 50 clones contained rice DNA (93.0%). Some of the clones (7%) contained no inserts. The DNA insert sizes ranged between 30 –250 kb with an average of 125 kb.

High molecular weight DNA used to construct the BAC library was isolated from purified rice nuclei. Most of the chloroplasts and mitochondria were removed by low speed centrifugation (<1000 g). The low frequency of chloroplast or mitochondrial clones found in the inventive BAC library (<0.3%) reduces the possibility of organellar/nuclear DNA co-ligation.

The BAC library was used to construct a contiguous set of clones (contig) spanning the Xa21 locus. Two Xa21-linked DNA markers, RG103 (1 kb, see, Ronald, et al. Mol. Gen. Genet. 236:113–120 (1992)) and pTA818 (1.2 kb, equivalent to RAPD818 in Ronald, et al.) were used to screen the BAC library. RG103 is found in 8 copies in the Xa21-containing line and hybridizes with 8 genomic HindIII DNA fragments in this line. All of these fragments are genetically and physically linked to the Xa21 disease resistance locus. pTA818 hybridizes with 2 DNA fragments and at least one of these fragments is linked to the Xa21 locus. Ronald, et al. (1992).

7296 BAC clones were probed-with pTA818 (2 copies) and RG103 (8 copies). Seven and five BAC clones hybridizing with RG103 and pTA818, respectively, were identified. BAC DNA was isolated from these clones and digested with HindIII. The DNA fragments were separated by PFGE. Southern analysis showed that the 7 RG103 hybridizing BAC clones carried 4 different copies of the RG103 genomic HindIII fragments. The probe was hybridized with a 4.3 kb DNA fragment and 9.5 kb fragment, a 9.6 kb fragment and a 6.2 kb fragment. The size of the DNA fragments are deduced from lambda DNA digested with HindIII.

Four BAC clones were isolated that carried one copy of the pTA818 HindIII fragment and one BAC clone was identified that contained the other copy. One of the pTA818 containing BACs also hybridized with the marker PTA248 (equivalent to RAPD248 in Ronald, et al. (1992), confirming that these two cloned RAPD markers are within 60 kb of each other. Ronald, et al. (1992).

The identification of 12 BAC clones hybridizing with 2 cloned DNA sequences (corresponding to 10 DNA fragments in the rice genome) is slightly lower than the 20 clones expected based on screening 2× genome equivalents (7296 clones, 450,000 kb genome, 125 kb average insert size). Specifically, the pTA818 sequences and four (out of eight) of the RG103 hybridizing sequences are over represented in this portion of the library. By contrast, the other four RG103 hybridizing sequences are under represented. The DNA insert sizes of these clones ranged from 40 to 140 kb.

Cosmid Clones

A. Materials and Methods

Preparation of high molecular weight (HMW) DNA from rice leaves

The rice line, 1188 carrying the Xa-21 locus, was used as the plant material for isolation of HMW DNA. 120 g 4–6 weeks old leaf tissue was harvested and ground into fine powder using a cold mortar and pestle in liquid nitrogen. The powder was then suspended by stirring in 800 ml cold H buffer [4 mM spermidine, 1 mM spermine, 10 mM EDTA, 10 mM Tris-HCl, 80 mM KCl, 0.5 M sucrose, 1 mM PMSF (phenylmethyl sulphonyl) fluoride, add just before use), 0.5% (v/v) Triton-X 100, 1/1000 (v/v) β-mercaptoethanol (add just before use), pH 9.5]. The mixture was filtered through an 80-micron sieve into GSA bottles and the pellet resuspended in 400 ml H buffer and filtered again. The two filtrate volumes were combined and centrifuged at 3500 rpm for 10 min at 4° C. The pellet was resuspended in 300 ml washing buffer (same as H buffer except PMSF and β-mercaptoethanol) and centrifuged at 3500 rpm for 10 min at 4° C. The pellet was washed two additional times until the color of the pellet was pale green. The pellet was resuspended in 40 ml washing solution and the nuclei were lysed by adding an equal volume of lysis buffer (2% Na laurel sarcosine, 100 mM Tris-HCl, 0.5 M EDTA, pH 9.5) containing 2 mg/ml proteinase K (Boehringer Mannheim). Proteins were removed by incubation at 50° C. for 5 hr and then extraction of the solution (by gentle inversion) with an equal volume of phenol-chloroform-isoamyl alcohol (24:24:1) for 30 min at room temperature. The HMW DNA was precipitated by gently layering 1/10 vol. of 3M sodium acetate (pH 5.5), 2 vol. of ethanol and inverting several times. Finally, the DNA was removed from the ethanol using wide-mouth pipette tips, washed with 70% ethanol, dried and dissolved into 1 ml of TE (10 mM Tris-HCl, 1 mM EDTA, pH8.0) at 4° C. overnight without shaking. Normally, 250 ug HMW DNA can be isolated from 120 g leaves.

Preparation of insertion DNA (A) Partial digestion of HMW DNA

Pilot experiment. 30 ug (70 ul) of HMW DNA was mixed with 10 ul of 10× Sau3AI buffer (NEB) and pre-warmed at 37° C. for 5 min. 20 ul (2 units) of Sau3AI was then added to the DNA solution, gently mixed with a wide-mouth pipette tip and incubated at 37° C. 15 ul aliquots were removed at 0, 5, 10, 20, 30 and 70 min and immediately mixed with 5 ul 0.5 M EDTA (pH8.0) on ice to stop the reaction. The samples were analyzed by electrophoresis through a 0.3% agarose/TBE gel at 2 V/cm gel length for 36 hr in the cold room.

Large-scale partial DNA digestion was achieved by repetition of the pilot experiment using the optimized incubation time intervals of 20 min at 37° C.

(B) Size-selection

The partially digested DNA was fractionated on a sucrose density gradient of S to 40% by centrifuge in an SW27 rotor at 26,000 rpm at 20° C. for 13 hr. 0.8 ml fractions (20 total) were collected by carefully placing a capillary tube at the bottom of the centrifuge tube and pumping out the gradient at a very slow speed. 20 ul of each samples was assayed on a 0.3% agarose gel at 2 V/cm gel length for 36 hr. DNA fractions with approximately 35–50 kb were pooled together. After diluting the sucrose with an equal vol. of H2O, the DNA was precipitated with 2 vol. ethanol. The partial fill in reaction was achieved using standard protocols.

Ligation, packaging and transfection

The cosmid vector, pHC80, was kindly provided by Dr. Scot Hulbert. Vector and insert DNA were ligated in a 2 to 1 molar ratio, at a final concentration of 0.8 ug/ul. The ligation reaction was carried out with 600 units of T4 DNA ligase (NEB, USA) at 16° C. for overnight. The ligated DNA was in vitro packaged with GigapackII packaging extract (Stratagene, USA) and transfected into competent cell, E. coli NM554, according to the Stratagene manual.

Library screening 61440 cosmid colonies (more than five genome equivalents) in 160 384-well microtiter plates were transferred onto Hybond N+ filters (Amersham, USA) in two type densities. In the first method, the cosmid clones were replicated in low density (1536 colonies/11.5×15 cm filter) using manual replicators (Genetix, U.K.) and grown on LB/agar with 100 ug/ml ampicillin for overnight. Forty filters were made to cover the whole cosmid library. In the second method, the cosmid clones were replicated in high density arrays using a Beckman Biomek™ robotic workstation and grown using the same method as above. Using 3×3 arrays, 3456 colonies were transferred onto an 8.5×12 cm filter. In order to exactly localize the positive colonies on a negative background, a reference cosmid colony (containing the RG103 marker) was plated in the first position of each 3×3 grid. The remaining eight offset position were plated with colonies from eight microtiter plates of the cosmid library. In this case, 20 filters in size of 8.5×12 cm each can cover the whole library. For hybridizations with a unique probe, the RG103 probe was mixed with the unique probe in a ratio of 1:4 to produce the reference pattern.

Bacteria on the filters were lysed and fixed using the steaming water bath procedure with the following modification: colonies were placed face up on top of two pieces of 3 MM Whatman soaked in lysis solution (0.5 M NaOH, 1.5 M NaCl) for 4 min at room temperature, the plastic boxes containing the filters were incubated in a steaming water bath at 85° C. for 6 min and then the filters were transferred to 3 MM Whatman soaked in neutralization buffer (1 M Tris-HCl (pH7.4), 1.5 M NaCl) for 4 min. Proteins and cell debris were removed by submergence in 50 ml proteinase K solution (50 mM Tris-HCl (pH8.5), 50 mM EDTA (pH8.0), 100 mM NaCl, 1% (w/v) Na-lauryl-sarcosine, 250 ug/ml proteinase K) and incubated at 37° C. for 20 min. The filters were gently washed in 2× SSC solution for S min at room temperature, dried and UV treated the filters at 10 cm for 2.5 min.

Hybridization was performed according to standard procedures as follows: filters were subjected to prehybridization solution (7% SDS, 0.5 M $Na_2PO_4$ (pH 7.2), 1 mM EDTA, 100 ug/ml ssDNA) at 65° C. for 2 hr to overnight. Probes were labeled using the random primer extension procedure and hybridization was performed at 65° C. with shaking overnight. The filters were washed briefly in (40 mM $Na_2PO_4$ (pH 7.2), 0.1% SDS) at room temperature and the filters were incubated in the same solution at 65° C. for 20 min with gentle shaking.

B. Results

Three Xa21-linked markers (RG103, RAPD 248 and RAPD 818) were used to screen the cosmid library. Genomic Southern analysis showed that the copy numbers of these three markers in resistant lines are 8, 1 and 2 respectively (unpublished results). Six positive cosmid clones hybridizing with the RG103 marker were identified and confirmed by further Southern analysis. However, no positive clones were identified to contain RAPD248 and RAPD818.

EXAMPLE 2

Characterization of the Xa21 Genes

Figure 2F:
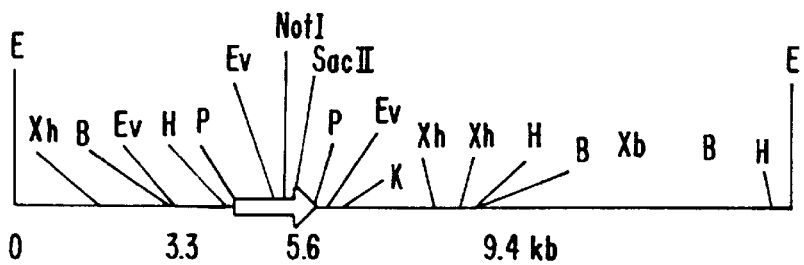

Five cosmid clones and 1 BAC clone isolated in Example 1 were further characterized by restriction enzyme mapping. FIGS. 2A–2E are partial restriction maps of the cosmid clones. FIG. 2F is a partial restriction map of the BAC clone.

An open reading frame in one of the clones, pB806, was identified (SEQ ID NO:1). It includes the promoter region, the predicted intron and a partial 3' sequence. SEQ ID NO:2 shows the predicted amino acid sequence. The predicted intron has been spliced out.

The predicted amino acid sequence has revealed two features of the protein which indicate it is encoded by a member of the new class of plant disease resistance genes referred to here as RRK genes. First, the extracellular domain of the proteins encoded by these genes comprise a block of about 23 tandem leucine-rich repeats (LRR) with an average length of 24 amino acids. The LRR motif has been implicated in protein-protein interactions and ligand binding in a variety of proteins. The extracellular domain also comprises a region between the LRRs and the signal peptide which contain a motif, SWNTS (SEQ ID NO:16), which is conserved among a number of proteins, including, Cf-9, PGIP, and RLK5. In addition, the protein comprises a region with high sequence identity to receptor-like protein kinases (RLPKs) such as RLK5 and TXK1 (Walker et al. *Plant J.* 3:451 (1993); Chang et al. *Plant Cell* 4:1263 (1992); Valon et al. *Plant Molec. Biol.* 23:415 (1993)) as well as the tomato resistance gene product, Pto (Martin et al. *Science* 262:1432 (1993). The signal domain, the extracellular domain (including the LRR region), the transmembrane domain and the cytoplasmic kinase domain are identified in SEQ ID NO:2.

Figure 3:
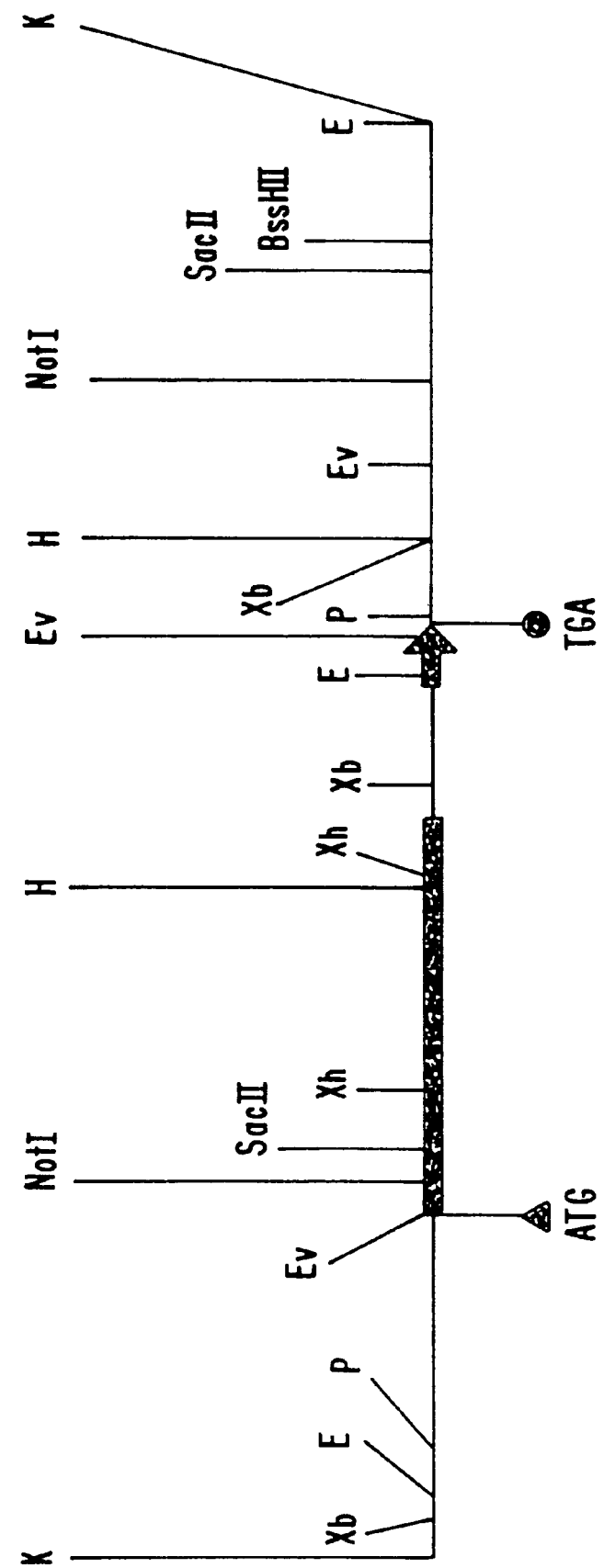
FIG. 3 shows a restriction map of pB822, the most active copy.
Figure 4:
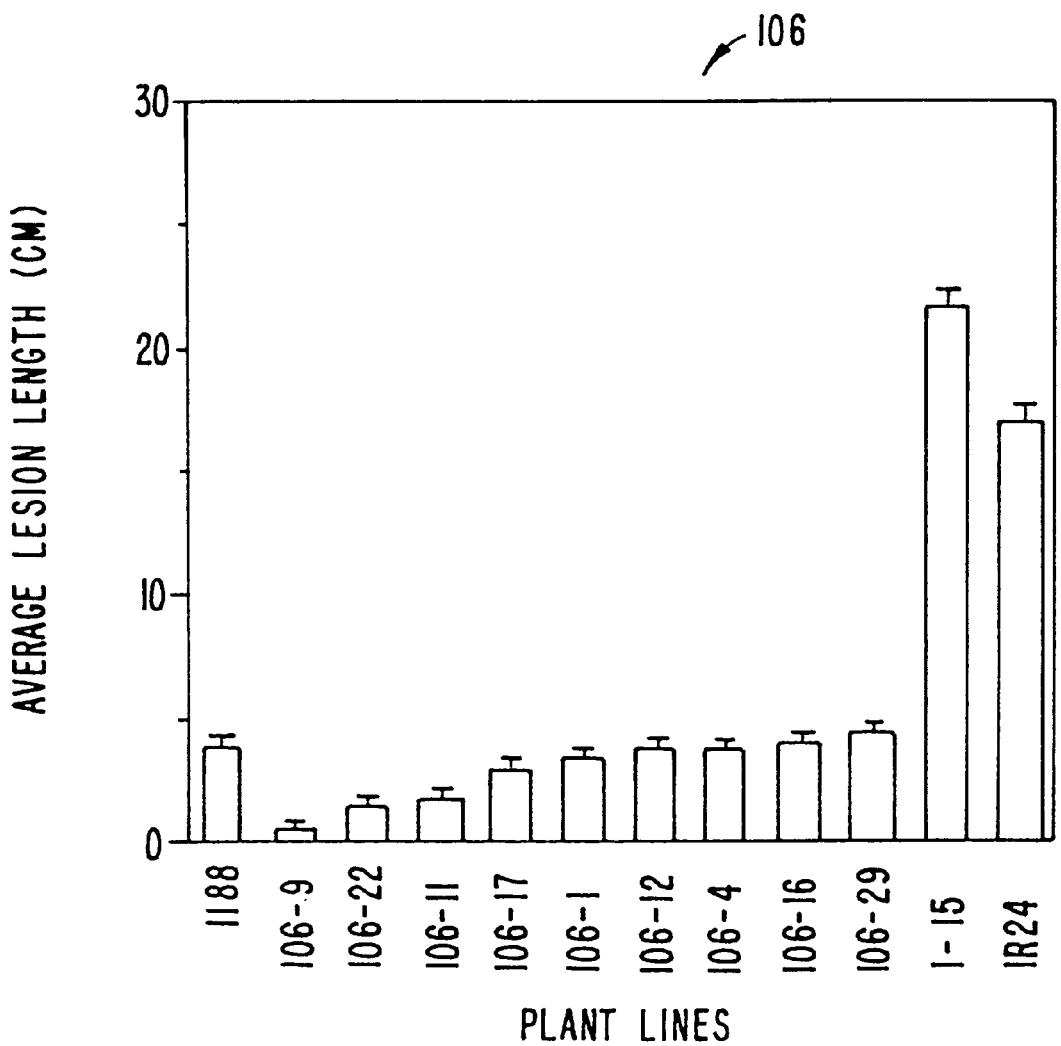
FIG. 4 shows the results of assays measuring Xanthomonas resistance in transgenic plants comprising the Xa21 gene from the pB822 clone.
Figure 5:
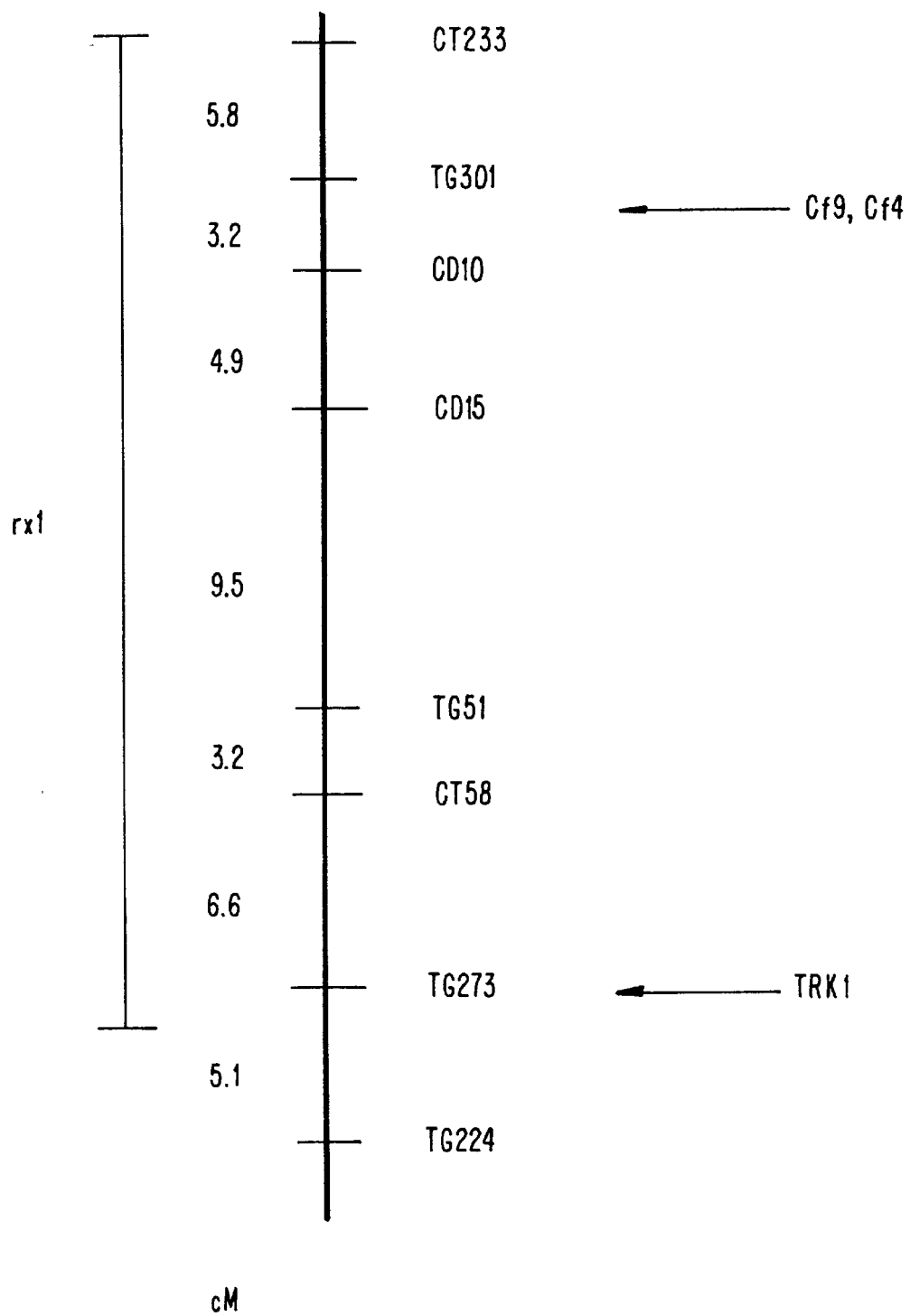
FIG. 5 shows the map position of TRK1.
Figure 6:
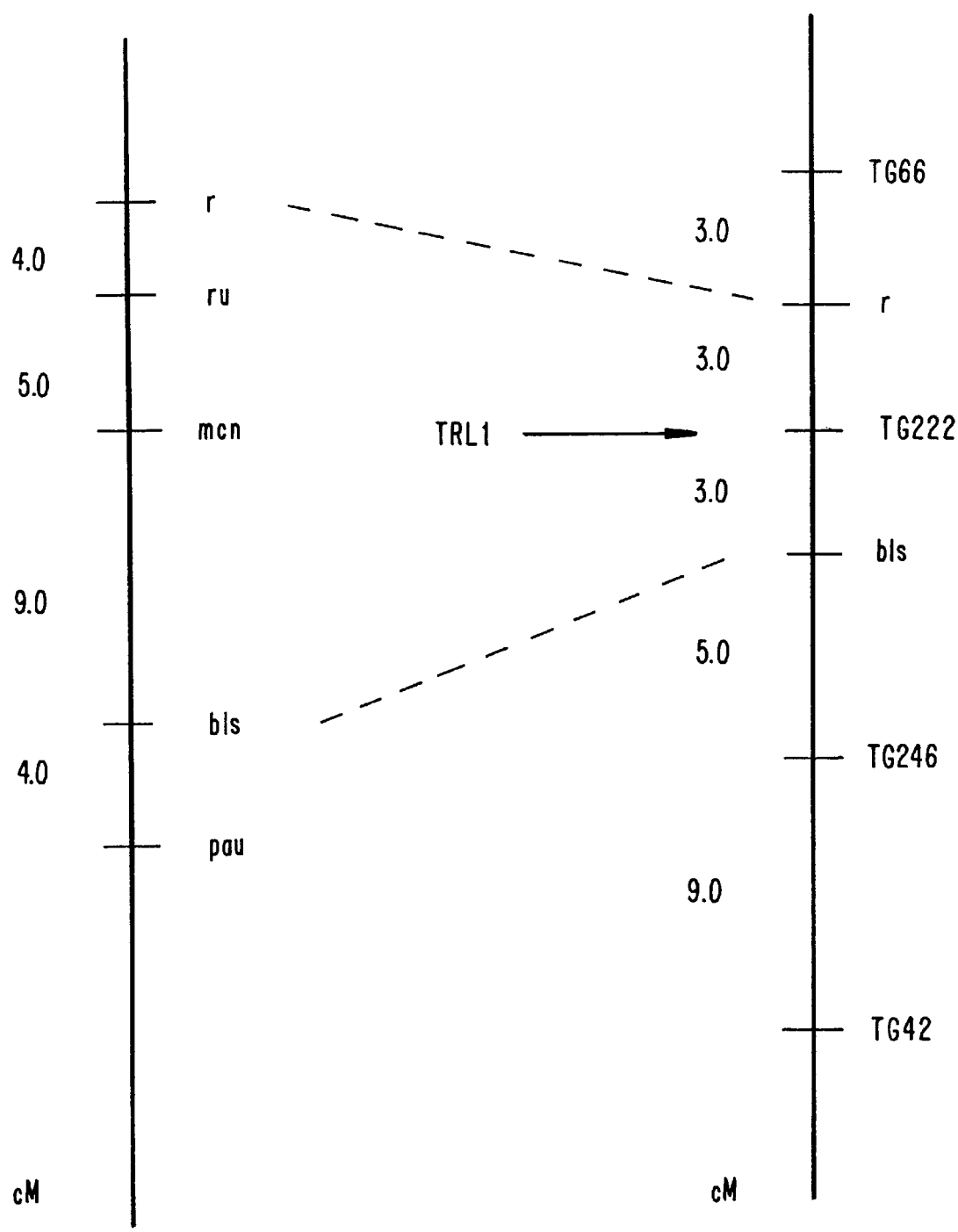
FIG. 6 shows the map position of TRL1.

FIG. 3 is a restriction map of a second clone, pB822, which was used to construct the plasmid used in the transformation experiments described in Example 3, below. The Xa21 gene in this clone has also been sequenced (SEQ ID NO:3). The predicted amino acid sequence (SEQ ID NO:4) revealed the same motifs identified in SEQ ID NO:2.

The protein kinase domain carries 11 subdomains containing 15 conserved residues diagnostic of protein kinases and is flanked by a 31 aa juxtamembrane domain (aa 677–707) and a C terminus domain. The presumed intron is located between the two highly conserved residues P and E (aa 892 and aa 893) in the putative catalytic domain. The consensus sequences present in subdomains VI (DIKSSN) (SEQ ID NO:17) and VIII (GTTGYAAPE) (SEQ ID NO:18) strongly suggest that Xa-21 has serine/threonine kinase (as opposed to tyrosine) activity.

Previous work has demonstrated that phosphorylated RLK5 protein interacts with the kinase interacting domain (KID) of a type 2C serine-threonine protein phosphatase (Stone et al., *Science* 266:793–795 (1994)). The KID binds the phosphorylated LRR containing proteins, RLK5 and TMK1, but fails to bind the S-related receptor kinases ZmpK1 and RLK4. These results suggests that the Arabidopsis KID is functionally analogous to the SH2 domain of animal proteins. Sequence alignment of the Arabidopsis receptor like kinases RLK5, TMK1 with Xa-21 reveals a set of conserved amino acids (N/Q)X(L/V)S(G/S)(L/A)(F/V) (P/E) (SEQ ID NO:19) surrounding a serine residue that is carboxy terminal to the last residue (arginine) highly conserved in all protein kinases (position 999 in Xa21 gene product). The carboxyl terminal position of this consensus in these proteins is similar to the carboxyl terminal phosphotyrosine of the Rous sarcoma virus oncogene product pp60 c-Src which is essential for binding to SH2 domain containing proteins. These conserved amino acids are lacking in the S related receptor kinases ZmpK1, RLK4 and SRK6 and in intracellular kinases which do not bind KID. Thus, this region act as a high affinity and specific binding site for proteins containing KID. Modification of the amino acid sequence of this region of Xa21 can thus be used to alter affinity for the KID protein and thus control intracellular signaling in response to ligand binding of the LRR domain.

EXAMPLE 3

Plant Transformation Using an Xa21 Gene

The Xa21 gene described above was used to transform rice plants to demonstrate that the genes could confer Xanthomonas resistance to susceptible plants. The gene was introduced into susceptible rice strains using a variation of the methods of Li et al., *Plant Cell Rep.* 12:250–255 (1993). Briefly, co-transformation was carried out using the hygromycin construct pMON410 (from Monsanto) and a bluescript vector containing the sequences of interest. In addition, the Kpn fragment of pB822 was cloned into the pTA818 vector, which is derived from Invitrogen vector pcr1000 and contains the 1 kb fragment RAPD818 (Ronald et al., supra). The resulting plasmid is referred to as pC822. The plants were selected on hygromycin (30 mg/L) and then screened for resistance to Xoo race 6.

Standard methods were used to test Xanthomonas resistance in the transformants. The assays were carried out according to the methods of Kaufman et at *Plant Disease Rep.* 57:537–541 (1973). Briefly, Xoo race 6 was grown on PSA plates for 3 days. The bacteria were scraped up, resuspended in water and the OD adjusted to $10^9$ colony forming units per ml. Scissors were dipped in the suspension and leaves from the transformed plants (4 months post bombardment) were cut 5 cm from the tip. Plants were scored for the presence of lesions 11 days post inoculation.

FIG. 4 shows lesion length data from experiments using an expression vector comprising the gene from the pC822 clone. Individuals derived from independent transformants 106, −9, −22, −11, −17, −1, −12, −4, 16, and −29 carry the pC822 construct and showed increased resistance as compared to susceptible untransformed controls (IR24), as well as rice plants transformed with the vector (1–15).

EXAMPLE 4

Isolation of RRK Genes from Tomato

As noted above the Xa21 sequence can be used to isolate RRK genes from other plant species using a degenerate primer or low stringency hybridization approach. This example describes the isolation and characterization of two RRK genes from tomato using a degenerate primer approach.

Degenerate primers were prepared so that the PCR (polymerase Chain Reaction) products should amplify between the LRR and kinase domains and therefore span the transmembrane domain. The forward primers were taken from motifs conserved in the LRR region of Xa21 and several other plant proteins (e.g., Cf-9, RLK5, and PGIP). The reverse primers were taken from motifs conserved in the Xa21 kinase domain and other plant serine-threonine kinase domains( e.g., RLK5, Pto, and Fen (Martin et al. *Plant Cell* 6:1543–1552 (1994)).

The degenerate primers used for amplification of PCR products were as follows:

1. LRR region

TCA AGC AAC AAT TTG TCA GGN CA(A/G) AT(A/T)TC (SEQ ID NO:5)

2. Kinase region

TAA CAG CAC ATT GCT TGA TTT NAN (G/A)TC NCG (G/A)TG (SEQ ID NO:6)

TAA CAG CAC ATT GCT TGA TTT NAN (G/A)TC (G/A)CA (G/A)TG (SEQ ID NO:7).

TAA CAG CAC ATT GCT TGA TTT NAN (G/A)TC (T/C)CT (G/A)TG (SEQ ID NO:8)

The PCR conditions were as follows (20 micro liter reaction):

First cycle

94 C. for 30 sec (denaturing)

55 C. for 30 sec (annealing)

72 C. for 1 min (extension)

For the next 19 cycles, the annealing temperature dropped down 1 C. every cycle. After the 20 cycles are finished, the reaction was incubated for 10 min at 72 C.

After the initial amplification using these degenerate primers, a second round of amplification was performed with the following specific primers:

TAAGCAACAATTTG (SEQ ID NO:22)

and

TAACAGCACATTGCTTGA (SEQ ID NO:23)

The conditions for this amplification was as follows:

35 cycles

94 C. for 15 sec

55 C. for 15 sec

72 C. for 15 sec

At the end of the 35 cycles, the reaction was incubated for 72 C. for 10 min

The PCR products were cloned and used as probes to a tomato cDNA library. The library was constructed from tomato cDNA that was primed with oligo DT primers, ligated to EcoRI adaptors and cloned into a lambda GT11 vector.

These primers were used to isolate two tomato PCR products and cDNAs belonging to the RRK family of disease resistance genes. The first clone TRK1 (Tomato Receptor Kinase 1) is a 250 bp PCR product and was used to isolate partial cDNAs. The DNA sequence is shown in SEQ ID NO:24. The deduced amino acid sequence of TRK1 is shown in SEQ ID NO:25.

This clone is present as one or two copies in the tomato genome and one copy maps to the short arm of chromosome 1 in the proximity of a resistance gene to *Xanthomonas campestris* pv. *vesicatoria* (Rx1) (Zu et al. *Genetics* 141:675–682 (1995)) (see, FIG. 5).

The second clone TRL1 (Tomato Receptor Like 1) is a 496 bp PCRproduct. The DNA sequence is shown in SEQ ID NO:26. The deduced amino acid sequence is SEQ ID NO:27. TRL1 maps within a few cM of mcn (see, FIG. 6) a mutation on chromosome 3 that causes spotty necrosis on plants, typical of a defense phenotype.

These results indicate that the Xa21 gene can be used to isolate RRK genes from other plant species. For example, the TRK1 and TRL1 genes that were isolated are important components of plant signal transduction pathways leading to a defense response. These genes are useful to engineer disease resistance in tomato and other plant species.

The above examples are provided to illustrate the invention but not to limit its scope. Other variants of the invention will be readily apparent to one of ordinary sill in the art and are encompassed by the appended claims. All publications, patents, and patent applications cited herein are hereby incorporated by reference.

RRK-F aagctttctaaattatttaactctaagtctgttattatccccaagtacatcatcatcatac SEQ ID NO:1
ataatatttcatattcacgacatccttaagctagatgcttttggccattctcttatctttt
taaagaaattctctcccaattaagatgagagtgtcttctagcaatttgccagttttacaa
tgtctttgagtcctcacacattttcatgatgttaccaataaattacggacgccgtgtttag
ttctaaagttttcttcaaacttacaacttttcaatcgcatcaaactttctcctacacac
acaaactttcaacttttccatcacatcgttccaatttcaaccaaacttccaattttggtat
gaactaaacacagccgaaaacaaaatctgtgtgttatggccctgtttagattctaacttttc
ccattacatcaaacttcctacatacacgaactttcaacttttccgtcacatcgtttcaat
tttttaaaacttccattttaacgtggaactaaacacaacctatataacggaatttgtcaa
aaactcaatggtgaaagtcacacctcacaggaagggcgcgctctagtcaagacatcattaa
acaggtacacaggttgtactagcttgtcatgtttatcttgcgtctgcgagacgtaaatcca
tgccaaacaaaagtgcttctatagagatatcataaggatatggtttggggccatatccaac
tgctcaggagagatctcgttcggaggtgaggttagatgttcacctctccacacataacgaa
ggcgatcttcttcgcatatgattaggcattagataaaataaccttaaaaaataaatcaata
tgatttttttagaaaaaaattatatacactaagtataagcattgtcaaggaggaacaaaca
cacactcccatatagagagatagaaacatagctataggtagtgtcactgagtattttccat
cacgcatatccatataaaattaggggtgttacatccataggtgtaaagttttggcatgtt
atatcgagtattacgtagaatgccgtattaggtgtccgggcactaataaaaaaataattac
agaatccgttagtaaaccgcgagataaatttattaagcctaattaatcccatcattaacaa
atgtttaccgtagcaccacattgtcaaatcatggagcaattaggtttaaaagattcgtctc
gcaaattagtcataatctgtgcaattagttatttttagactatatttaagacttcgtacag
gtgttcaaacgttcgatgtgacatggtgcaaaattttagggtgtcatctagacactcctt
aattagaaagttaggaagaggcggtaaagaacgcagcatgactgaaactttgaaaattga
taaggtacaccaactggagtatctttatttcattgaagactttgaccagaagagcttga
cccgttttcttggagtagccagtaatgtttcattcttttccttttgctgggacttctttt
tattttttttgacaggagccatttgtttgggacttgggatccctttactgttataggaccag
tgcttgaatccaaacactgcattgatcagctcagctcattgtagcgcactcctccgcatgc
ATGGCGAGATCACCAACGTCGGTCATGATCTCTTCTTTGCTGCTGCTGCTGTTGATCGGCC
CAGCGAGCAGTGACGATGATGCTGCTGCTGCTGCTGCTCGTACCAGTACAGGCGGCGTCGC
GGCGACGAACTCGCGCTGCTCTCTTTCAAGTCATCCCTGCTACACCAGGGGGGCTTGTACG
CTGGCATCTTGGAACACGTCCGGCCACGGCCAGCACTGCACATGGGTGGGTGTTGTGTGCG
GCCGCGCGCCGGCACCCACACAGGGTGGTGAAGCTGCTGCTGCGCTCGTCCAACCTGTC
CGGGATCATCTCGCCGTCGCTGGGCAACCTGTCCTTCCTCAGGGAGCTGGACCTCAGCGAC
AACTACCTCTCCGGCGAGATACCACCGGAGCTCAGCCGTCTCAGCAGGCTTCAGCTGCTGG
AGCTGAGCGGTAACTCCATCCAAGGGAGCATCCACGCGGCCATTGGAGCATGCACCAAGTT
GACATCGCTAGACCTCAGCCACAACCAACTGAGATTGGTGCCAGCTGAAACATCTCTCGAA
TTTGTACCTTCACACCAATGGTTATGTCAGGAGAGATTCCATCTGATTTTGGGCAATCTCA
CTACGCCTTCAGTATTTGATTTGACCTGCAACAGATTATCACGGAGCTATACCTTCATCGC
TAGGGCAGCTCAGCAGCAGTCTATTGACTATGAATTTTGTGCTACGAACAATCTAACTGGC
ATGATCCCCAATTCTATCTGGAACCTTTCGTCTCTAGCAGCGTTTAGCTGTCAAGCGAAAA

```
ACAAGCTAGGTGGTATGATCCCTACAAATGCATTCAAAACCCTTCACCTCCTCGAGGTGGT
AGATATGGGCACTAACCGATTCCATGGCAAAATCCCTGCCTCAGTTGCTAATGCTTCTCAT
CTGACACGGCTTCAGATTGATGGCAACTTGTTCAGTGGAATTATCACCTCGGGGTTTGGAA
GGTTAAGAAATCTCACAACACTGTATCTCTGGAGAAATTTGTTTCAAACTAGAGAACAAGA
AGATTGGGGGTTCATTTCTGACCTAACAAATTGCTCCAAATTACAAACATTGGACTTGGGA
GAAAATAACCTGGGGGGAGTTCTTCCTAATTCGTTTTCCAATCTTTCCACTTCGCTTAGTT
TTCTTGCACTTGATTTGAATAAGATCACAGGAAGCATTCCAAAGGATATTGGCAATCTTAT
TGGCTTACAACATCTCTATCTCTGCAACAACAATTTCAGAGGGTCACTTCCATCATCGTTG
GGCAGGCTTAGAAACTTAGGCATTCTAGTCGCCTACGAAAACAACTTGAGCGGTTCGATCC
CATTGGCCATAGGAAATCTTACTGAACTTAATATCTTACTGCTCGGCACCAACAAATTCAG
TGGTTGGATACCATACACACTCTCAAACCTCACAAACTTGTTGTCATTAGGCCTCTCGCAC
CTCGCACCACAATCAGGGTTGGATACCTACACATCTCAACCTCACAACTGTGTCATAGCCT
TCACTATACCTAGTGGGTCCCAAATACCCCAGGTGAAATTAATTCAAATAGTCCAAACACC
TATCAAAAAGATGATCAATGTATCAAAAAATACACTTGGAGGGATCAGATACCCACAAGAA
ATAGGGCATCTCAAAAATCTAGTAGAATTCATGCAGAATCGAATAGATATCAGTAAAATCC
CTAACACGCTTGGTGATTGCCAGCTCTTACGGTATCTTTATCTGCAAAATAATTTGTTATC
TGGTAGCATCCCATCAGCCTTGGGTCAGCTGAAAGGTCTCGAAACTCTTGATCTCTCAAGC
AACAATTTGTCAGGCCAGATACCCACATCCCTTAGCAGATATTACTATGCTTCATTCCTTG
AACCTTTCTTTCAACAGCTTTGTGGGGAAGTGCCAACCATTGCGTGCTTTCGCAGATGCA
TCCGGGATCTCAATCCAAGGCAATGCCAAACTCTGTGGTGGAATACCTGATCTACATCTGC
CTCGATGTTGTCCCATTACTAGAGAACAGAAAGCATTTTCCAGCTCTACCTATTTCTGTTT
CTCTGGTCGCAGCACTGGCCATCCTCTCATCACTCTACTTGCTTATAACCTGGAACAAGAG
AACTAAAAAGGGAGCCCCTTCAAGAACTTCCATGAAAGGCCACCCATTGGTCTCTTATCCG
CAGTTGGTAAAAGCAACAGATGGTTTCGCGCCGACCAATTTGTTGGGTTCTGGATCATTTG
CCTCAGTATACAAACGAAAGCTTGAAAATCCTAAGGCACTCAAGAGTTTCACTGCCGAATG
TGAAGCACTACGAAATATGCGACATCGAAATCTTGTCAAGATAGTTACAATTTGCTCGAGC
ATTGATAACAGAGGGAACGATTTCAAAGCAATTGTGTATGACTTCATGCCCAACGGCAGTC
TGGAAGATTGGATACACCCTGAAACAAATGATCAAGCAGACCAGAGGCACTTGAATCTGCA
TCGAAGAGTGACCATACTACTTGATGTTGCCTGTGCATTGGACTATCTTCACCGCCATGGC
CCTGAACCTGTTGTACACTGTGATGTTAAATCAAGCAATGTGCTGTTAGATTCTGATATGG
TAGCGCATGTTGGAGATTCTGGGCTTGCAAGAATACTTGTTGATGGGACCTCATTGATACA
ACAGTCAACAAGCTCGATGGGATTTAGAGGGACAATTGGCTATGCAGCACCAggtcagcaa
gtccttccagtattttgcattttctgatctctagtgctatatgaaatagtttttacctcta
gtgaaactgatggagaatataagtaattaattgaactaattaaattgcacaaaaataagat
tatttgccatatctattcagatgctaaatatagctagttcatagaggtacatattttttt
atataggaatctagagctactacacactcaaatcaaattatgggtgttttctgctctacac
tgcaatatgaaatgattatcagaaggatcaaatttgagtaaatttgtcaattctacattta
agaaacactttttttgtatgtactagttattacaattttttatttcaagaacttgcattg
accatgaaaagtacttggtactacttctaattcccacatggaggtggtgaaaataatatag
atacaaaaacgaagtatcatatgttgtgtgatatactataatcacaatgaacacaaacagg
```

-continued

```
attcgtacaaaagtaattggccatcatagcaactgattgcttggggtaactgtatagcaca atcataccaaatttctttagatatgtatttgtaaattagattcttaaagttaaatatgaaa tttcattggtatttatgtttctttatataataaaaattaatccaacctttacatctaccat ttgtccagccatccttgttatttgtgatatttaacacgtaattttacataattatacatcc aagttcttttatttaacactggaaatttgaaatcgtatttcctactcaaacaGAGTATGG

CGTCGGGCACATTGCATCAACACATGGAGATATTTACAGCTATGGAATTCTAGTGCTGGAA

ATAGTAACCGGGAAGCGGCCAACTGACAGTACATTCAGACCCGATTTGGGCCTCCGTCAGT

ACGTTGAACTGGGCCTACATGGCAGAGTGACGGATGTTGTTGACACGAAGCTCATTTTGGA

TTCTGAGAACTGGCTGAACAGTACAAATAATTCTCCATGTAGAAGAATCACTGAATGCATT

GTTTCGCTGCTTAGACTTGGGTTGTCTTGCTCTCAGGATTTNCCATTGAGTAGACGCCACC

CGGAGATATCACCGACGAACTGAatgccatcaaacagaatctctccggagttgtttccagt gtgtgaaggtgcgagcctcgaattctgatgttatgtcttgtaatgttttattgccactagt cttcagattggaatgctcttccgatcagacttcttcagtggtatctaccacacgatcacta aagtcatcgtggctatttcctgatccagcatatctgatcatgcatgttctgtgttttatac ctgtatttactctgaattgccacacctcaaccctgcctctgtttgtttggcatacaaaag atagtgatgagtatattgtttcagggcttcctagttggcgtgtgtgcttaccggcacgca cgcagcccgagggtgggtttctttttttttccattgttattccgttgctttttccaccac ggtagattttttttttctggatttccatttttccgttgttttctctatcgcttatgctg gcggatttttttccgtggttttttttcaagacgagtatatctaatgtaactaacatgtta cttttagataacgatggttattaagataagattttttctggaagattttttgtaagtaaat ggtaaaaatatggaaatggaaacggaaatagttttgctgttataccgatcgtttccatat ttaccgtattcttatagaaattaccgtntcttataatatggtaattaccgtatttctaaat atgttgatatcgattttgctatatatttgtcgac
```

RRK-F

MARSPTSVMISSLLLLLIGPASS          SEQ ID NO:2

DDDAAAAAARTSTGGVAATNSRCSLSSHPCYTRG

ACTLASWNTSGHGQHCTWVGVVCGRARRHPHRVVK

LLLRSS N LSGIISPS

LGNLSFLRELDLSD NYLSGEIPPE

LSRLSRLQLLELSG NSIQGSIHAA

IGACTKLTSLDLSH NQLRLVPAET

SLEFVPSHQWLCQERFHLI

LGNLTTPSVFDLTC NRLSRSYTFIAR

AAQQQSIDYEFCAT NNLTGMIPNS

IWNLSSLAAFSCQAKNKLGGMIPTNA

FKTLHLLEVVDMGT NRFHGKIPAS

VANASHLTRLQIDG NLFSGIITSG

FGRLRNLTTLYLWR NLFQTREQEDWGFISD

LTNCSKLQTLDLGE NNLGGVLPNSF

SNLSTSLSFLALDL NKITGSIPKD

IGNLIGLQHLYLCN NNFRGSLPSS

LGRLRNLGILVAYE NNLSGSIPLA

IGNLTELNILLLGT NKFSGWIPYT

LSNLTNLLSLGLSHLAPQSGLD

TYTSQPHNCVIAFTIPS GSQIPQVKLIQ

IVQTPIKKMINVSK NTLGG IRYPQE

IGHLKNLVEFMQNRID ISK IPNT

LGDCQLLRYLYLQN NLLSGSIPSA

LGQLKGLETLDLSS NNLSGQIPTS

LSRYYYASFLEPFFQQLCGGS

ANHCVLSQMHPGSQSKAMPNSVV

EYLIYICLDVVPLLENKKH

FPALPISVSLVAALAILSSLYLLITWN

KRTKKG

APSRTSMKGHPLVSYPQLVKATDGFAPTNLLGSGSFASVYKRKLENPKALKSFTAECEALR

NMRHRNLVKIVTICSSIDNRGNDFKAIVYDFMPNGSLEDWIHPETNDQADQRHLNLHRRVT

ILLDVACALDYLHRHGPEPVVHC<u>DVKSSN</u>VLLDSDMVAHVGDSGLARILVDGTSLIQQSTS

SMGFR<u>GTIGYAAPE</u>YGVGHIASTHGDIYSYGILVLEIVTGKRPTDSTFRPDLGLRQYVELG

LHGRVTDVVDTKLILDSENWLNSTNNSPCRRITECIVSLLRLGLSCSQDL*(F)PLSRRHF

EISPTNZ

\* L: "N" = "G"

F: "N" = "C"

ORF 3918 [3075 bp interupted by one intron (843 bp)]

ATGATATCACTCCCATTATTGCTCTTCGTCCTGTTGTTCTCTGCGCTGCTGCTCTGCCCTTCAAGCAGTGACGACG    SEQ ID NO:3

ATGGTGATGCTGCCGGCGACGAACTCGCGCTGCTCTCTTTCAAGTCATCCCTGCTATACCAGGGGGGCCAGTCGCT

GGCATCTTGGAACACGTCCGGCCACGGCCAGCACTGCACATGGGTGGGTGTTGTGTGCGGCCGCCGCCGCCGCCGG

CACCCACACAGGGTGGTGAAGCTGCTGCTGCGCTCCTCCAACCTGTCCGGGATCATCTCGCCGTCGCTCGGCAACC

TGTCCTTCCTCAGGGAGCTGGACCTCGGCGACAACTACCTCTCCGGCGAGATACCACCGGAGCTCAGCCGTCTCAG

CAGGCTTCAGCTGCTGGAGCTGAGCGATAACTCCATCCAAGGGAGCATCCCCGCGGCCATTGGAGCATGCACCAAG

TTGACATCGCTAGACCTCAGCCACAACCAACTGCGAGGTATGATCCCACGTGAGATTGGTGCCAGCTTGAAACATC

TCTCGAATTTGTACCTTTACAAAAATGGTTTGTCAGGAGAGATTCCATCCGCTTTGGGCAATCTCACTAGCCTCCA

GGAGTTTGATTTGAGCTTCAACAGATTATCAGGAGCTATACCTTCATCACTGGGGCAGCTCAGCAGTCTATTGACT

ATGAATTTGGGACAGAACAATCTAAGTGGATGATCCCCAATTCTATCTGGAACCTTTCGTCTCTAAGAGCGTTTA

GTGTCAGAGAAAACAAGCTAGGTGGTATGATCCCTACAAATGCATTCAAAACCCTTCACCTCCTCGAGGTGATAGA

TATGGGCACTAACCGTTTCCATGGCAAAATCCCTGCCTCAGTTGCTAATGCTTCTCATTTGACAGTGATTCAGATT

TATGGCAACTTGTTCAGTGGAATTATCACCTCGGGGTTTGGAAGGTTAAGAAATCTCACAGAACTGTATCTCTGGA

GAAATTTGTTTCAAACTAGAGAACAAGATGATTGGGGGTTCATTTCTGACCTAACAAATTGCTCCAAATTACAAAC

ATTGAACTTGGGAGAAAATAACCTGGGGGGAGTTCTTCCTAATTCGTTTTCCAATCTTTCCACTTCGCTTAGTTTT

CTTGCACTTGAATTGAATAAGATCACAGGAAGCATTCCGAAGGATATTGGCAATCTTATTGGCTTACAACATCTCT

ATCTCTGCAACAACAATTTCAGAGGGTCTCTTCCATCATCGTTGGGCAGGCTTAAAAACTTAGGCATTCTACTCGC

```
CTACGAAAACAACTTGAGCGGTTCGATCCCGTTGGCCATAGGAAATCTTACTGAACTTAATATCTTACTGCTCGGC

ACCAACAAATTCAGTGGTTGGATACCATACACACTCTCAAACCTCACAAACTTGTTGTCATTAGGCCTTTCAACTA

ATAACCTTAGTGGTCCAATACCCAGTGAATTATTCAATATTCAAACACTATCAATAATGATCAATGTATCAAAAAA

TAACTTGGAGGGATCAATACCACAAGAAATAGGGCATCTCAAAAATCTAGTAGAATTTCATGCAGAATCGAATAGA

TTATCAGGTAAAATCCCTAACACGCTTGGTGATTGCCAGCTCTTACGGTATCTTTATCTGCAAAATAATTTGTTAT

CTGGTAGCATCCCATCAGCCTTGGGTCAGCTGAAAGGTCTCGAAACTCTTGATCTCTCAAGCAACAATTTGTCAGG

CCAGATACCCACATCCTTAGCAGATATTACTATGCTTCATTCCTTGAACCTTTCTTTCAACAGCTTTGTGGGGGAA

GTGCCAACCATTGGTGCTTTCGCAGCTGCATCCGGGATCTCAATCCAAGGCAATGCCAAACTCTGTGGTGGAATAC

CTGATCTACATCTGCCTCGATGTTGTCCATTACTAGAGAACAGAAAACATTTCCCAGTTCTACCTATTTCTGTTTC

TCTGGCCGCAGCACTGGCCATCCTCTCATCACTCTACTTGCTTATAACCTGGCACAAGAGAACTAAAAAGGGAGCC

CCTTCAAGAACTTCCATGAAAGGCCACCCATTGGTCTCTTATTCGCAGTTGGTAAAAGCAACAGATGGTTTCGCGC

CGACCAATTTGTTGGGTTCTGGATCATTTGGCTCAGTATACAAAGGAAAGCTTAATATCCAAGATCATGTTGCAGT

GAAGGTACTAAAGCTTGAAAATCCTAAGGCGCTCAAGAGTTTCACTGCCGAATGTGAAGCACTACGAAATATGCGA

CATCGAAATCTTGTCAAGATAGTTACAATTTGCTCGAGCATTGATAACAGAGGGAACGATTTCAAAGCAATTGTGT

ATGACTTCATGCCCAACGGCAGTCTGGAAGATTGGATACACCCTGAAACAAATGATCAAGCAGACCAGAGGCACTT

GAATCTGCATCGAAGAGTGACCATACTACTTGATGTTGCCTGCGCACTGGACTATCTTCACCGCCATGGCCCTGAA

CCTGTTGTACACTGTGATATTAAATCAAGCAATGTGCTGTTAGATTCTGATATGGTAGCCCATGTTGGAGATTTTG

GGCTTGCAAGAATACTTGTTGATGGGACCTCATTGATACAACAGTCAACAAGCTCGATGGGATTTATAGGGACAAT

TGGCTATGCAGCACCAGGTCAGCAAGTCCTTCCAGTATTTTGCATTTTCTGATCTCTAGTGCTATATGAAATAGTT

TTTACCTCTAGTGAAACTGATGGAGAATATAAGTAATTAATTGAACTAATTAAATTGCACAAAAATAAGATTATTT

GCCATATCTATTCAGATGCTAAATATAGCTAGTTCATAGAGGTACAGATTTTTTTATATAGGACTCTAGAGCTACC

ACACACTCAAATCAAATTATGGGTGTTTTCTGCTCTACACTGCAATATGAAATGATTATTACTTCTACATGAACTG

ATGGAGGAGTTTCAGAAGGATCAAATTTGAGTAAATTTTTTCAATTCTACATTTAAGAAACACTTTTTTTTCATAT

GCTAGTTACATTTTTTTATTTCACGAGCTTACATTGACCATGAAAAATACTTGGCACTACTTACTAATTCCCACAT

GGAGGTAGTGAAAATAATATAGATACAAAAACGAAATATCCTATGTTGTGTGATATACTATAATCACAATGAACAC

AAACAGGATTCGTACAAAAGTAATTAGCCATCATAGCAACTGATTGCTTGGGGTAACTGTATAGCACAATCATACC

AAATTTCTTTAGATATGTATCTGTAAATTAGATTCTTAAAGTTAAATATGAAATTTCATTGGTATTTATGTTTCTT

TATATAATAAAAATTAATCCAGCCTTTGCATCTATCATTTGTCCAGACATCCTTGTTATTTGTGATATTTAACACG

TAAATTTACATAATTATACATCCAAGTTCTTTTTATTTAACACTGTAAATTTCAAATCGTACATGTTATAAAGAAT

GTACTATATTTCCTGCTCAAACAGAGTATGGCGTTGGGCTCATTGCATCAACGCATGGAGATATTTACAGCTATGG

AATTCTAGTGCTGGAAATAGTAACCGGGAAGCGGCCAACTGACAGTACATTCAGACCCGATTTGGGCCTCCGTCAG

TACGTTGAACTGGGCCTACATGGCAGAGTGACGGATGTTGTTGACACGAAGCTCATTTTGGATTCTGAGAACTGGC

TGAACAGTACAAATAATTCTCCATGTAGAAGAATCACTGAATGCATTGTTTGGCTGCTTAGACTTGGGTTGTCTTG

CTCTCAGGAATTGCCATCGAGTAGAACGCCAACCGGAGATATCATCGACGAACTGAATGCCATCAAACAGAATCTC

TCCGGATTGTTTCCAGTGTGTGAAGGTGGGAGCCTTGAATTCTGA
```

1025 amino acids

| | | | |
|---|---|---|---|
| A | MISLPLLLFVLLFSALLLCPSSS | 23 | SEQ ID NO:4 |
| B | DDDGDAAGDELALLSFKSSLLYQGGQSLASWN | 55 | |
| | TSGHGQHCTWVGVVCGRRRRRHPHR | 80 | |
| C | VVK LLLRSSN LSGIISPS | 98 | |

```
   LGNLSFLRE LDLGDNY LSGEIPPE          122
   LSRLSRLQL LELSDNS IQGSIPAA          146
   IGACTKLTS LDLSHNQ LRGMIPREI         171
   GASLKHLSN LYLYKNG LSGEIPSA          195
   LGNLTSLQE FDLSFNR LSGAIPSS          219
   LGQLSSLLT MNLGQNN LSGMIPNS          243
   IWNLSSLRA FSVRENK LGGMIPTNA         268
   FKTLHLLEV IDMGTNR FHGKIPAS          292
   VANASHLTV IQIYGNL FSGIITSG          316
   FGRLRNLTE LYLWRNL FQTREQDDWGFISD    346
   LTNCSKLQT LNLGENN LGGVLPNSF         371
   SNLSTSLSF LALELNK ITGSIPKD          395
   IGNLIGLQH LYLCNNN FRGSLPSS          419
   LGRLKNLGI LLAYENN LSGSIPLA          443
   IGNLTELNI LLLGTNK FSGWIPYT          467
   LSNLTNLLS LGLSTNN LSGPIPSE          491
   LFNIQTLSIMINVSKNN LEGSIPQE          516
   IGHLKNLVE FHAESNR LSGKIPNT          540
   LGDCQLLRY LYLQNNL LSGSIPSA          564
   LGQLKGLET LDLSSNN LSGQIPTS          588
   LADITMLHS LNLSFNS FVGEVPT           611
   IGAFAAASG ISIQGNAKLCGGIP            634
D  DLHLPRCCPLLENRKH                   650
E  FPVLPISVSLAAALAILSSLYLLITW         676
F  HKRTKK                             682
G  GAPSRTSMKGHPLVSYSQLVKATDG          707
H  FAPTNLLGSGSFGSVYKGKLNIQDHVAVKVLKLENPKALKSFTA 751
   ECEALRNMRHRNLVKIVTICSSIDNRGNDFKAIVYDFMPNGSLE 795
   DWIHPETNDQADQRHLNLHRRVTILLDVACALDYLRHGPEPVV  839
   HCDIKSSNVLLDSDMVAHVGDFGLARILVDGTSLIQQSTS     879
   SMGFIGTIGYAAP/EYGVGLIASTHGDIYSYGILVLEI       916
   VTGKRPTDSTFRPDLGLRQYVELGLHGRVTDVVDTKLILDSENW 960
   LNSTNNSPCRRITECIVWLLRLGLSCSQELPSSRTPTGDIIDEL 1004
I  NAIKQNLSGLFPVCEGGSLEF              1025

TCAAGCAACAATTTGTCAGGNCA A/G AT A/C/T CC              SEQ ID NO:5

TAACAGCACATTGCTTGATTTNAN G/A TCNCG G/A TG            SEQ ID NO:7

TAA CAG CAC ATT GCT TGA TTT NAN (G/A)TC (G/A)CA (G/A)TG  SEQ ID NO:20

TAA CAG CAC ATT GCT TGA TTT NAN (G/A)TC (T/C)CT (G/A)TG  SEQ ID NO:21

TAAGCAACAATTTG                                       SEQ ID NO:22
```

```
TAACAGCACATTGCTTGA                              SEQ ID NO:23

TRK1 open reading frame (DNA sequence)          SEQ ID NO:24

TCGACGTCGAACAATCGCTTGTCTGGTGCACTTCCTAGTGCTATTGGAAA

CTATTCAGGGCTGAAGAATCTTGTGTTAACTGGAAATGGTTTCTCAGGTG

ATATCCCTTCTGATATTGGCAGACTAAAGAGCATCTTAAAGCTGGACCTG

AGTAGAAACAACTTCTCTGGCACAATCCCTCCTCAGATTGGTAACTGTCT

TTCCTTAACTTACTTGGATTTGAGCCAAAATCAACTTTCTGGTCCTATCC

CAGTTCAAATTGCTCAAATTCACATCTTAAATTACATCAATATTTCCTGG

AATCACTTCAACGAGAGCCTTCCCGCGGAGATTGGCTTGATGAAGAGTTT

AACTTCAGCAGATTTTTCCCACAATAACTTATCTGGATCAATACCTGAAA

CAGGCCAATATTTATATTTCAACTCAACTTCCTTCACCGGCAACCCTTAT

CTCTCTGGATCCGACTCGACTCCTAGCAACATTACATCCAACTCACCGTC

AGAACTTGGAGACGGAAGTGACAGCAGAACTAAGGTTCCTACAATATACA

AGTTCATATTTGCATTTGGGCTCTTATTCTGCTCCCTCATTTTCGTTGTC

TTAGCAATAATCAAGACAAGAAAGGGGAGTAAGAATTCAAATTTGTGGAA

GCTGACAGCATTTCAGAAGCTTGAGTTCGGAAGTGAAGACGTCTTGCAGT

GCTTGAAAGACAACAACGTCATAGGGAGAGGTGGAGCAGGGATAGTGTAT

AAGGGAACTATGCCAAATGGTGATCATGTCGCGGTGAAGAAATTGGGAAT

AAGCAAAGGCTCACATGATAACGGCCTATCTGCTGAACTTAACACATTAG

GGAAGATCAGGCATAGGTACATTGTGAGACTGCTCGCGTTTTGTTCAAAC

AAGGAAGTCAACTTGCTAGTTTATGAGTACATGCTAAATGGAAGCTTAGG

TGAAGTGCTTCATGGGAAGAACGGCGGGCAACTCCAATGGGAAACTAGGC

TAAAAATAGCCATAGAAGCTGCCAAGGGCCTTTCTTATTTGCACCACGAT

TGCTCCCCTATGATAATCCACCGCGATGTCAAGTCCAACAATATATTGTT

GAACTCTGAACTTGAAGCTCATGTTGCAGATTTTGGATTAGCCAAGTACT

TTCGTAACAATGGTACCTCTGAGTGCATGTCTGCAATTGCAGGATCTTAT

GGCTACATTGCTCCAGAATATGCATACACGCTGAAAATTGATGAGAAAAG

CGATGTGTATAGCTTTGGAGTGGTGTTGTTGGAGCTTATAACAGGACGAA

GGCCAGTAGGAAATTTTGGAGAAGAAGGAATGGACATTGTACAATGGGCG

AAAACGGAGACAAAATGGAGCAAAGAAGGGGTGGTGAAAATCTTGGATGA

GAGGCTAAAAAATGTTGCAATTGTTGAAGCTATGCAAGTATTTTTTGTAG

CAATGCTTTGTGTTGAAGAGTACAGCATTGAGAGGCCTACAATGAGGGAA

GTAGTCCAAATGCTTTCTCAAGCTAAACAACCAAATACTTTCCAAATCCA

ATAA

STSNNRLSGALPSAIGNYSGLKNLVLTGNGFSGDIPSDIGRLKSILKLDLSRNNFSGTI    SEQ ID NO:25

PPQIGNCLSLTYLDLSQNQLSGPIPVQIAQIHILNYINISWNHFNESLPAEIGLMKSLT

SADFSHNNLSGSIPETGQYLYFNSTSFTGNPYLSGSDSTPSNITSNSPSELGDGSDSRT

KVPTIYKFIFAFGLLFCSLIFVVLAIIKTRKGSKNSNLWKLTAFQKLEFGSEDVLQCL
```

-continued

KDNNVGRGGAGIVYKGTMPNGDHVARSAGFAAASSRGGIVYKGTMPNGDHVAVK

KLGISKGSHDNGLSAELNTLGKIRHRYIVRLLAFCSNKEVNLLVYEYMLNGSLGEV

LHGKNGGQLQWETRLKIAIEAAKGLSYLHHDCSPMIIHRDVKSNNILLNSELEAHV

ADFGLAKYFRNNGTSECMSAIAGSYGYIAPEYAYTLKIDEKSDVYSFGVVLLELITG

RRPVGNFGEEGMDIVQWAKTETKWSKEGVVKILDERLKNVAIVEAMQVFFVAML

CVEEYSIERPTMREVVQMLSQAKQPNTFQIQ

TRL1 DNA sequence　　　　　　　　　　　　SEQ ID NO:26

TCAAGCAACAATTTRTCAGGACAAATACCTTCAGGCTTGGCCAATGTGAC

CACACTGGCAGCATTTAACGTTTCTTTCAATAATCTGTCTGGGCCACTGC

CTCTTAACAAAGATTTGATGAAGTGTAATAGTGTTCAGGGAAACCCCTTT

CTGCAATCGTGCCATGTATTTTCTCTATCAACACCTTCTACAGATCAGCA

GGGAAGAATAGGGGACTCACAAGATTCTGCTGCGTCTCCTTCAGGTTCAA

CCCAGAAAGGAGGGTGCAGCGGTTTCAACTCCATAGAGATTGCATCCATA

ACATCTGCGGCAGCTATTGTGTCAGTTCTTCTTGCTCTGATAGTCCTGTT

CTTTTACACCAGAAAATGGAATCCAAGATCTAGAGTTGCTGGATCTACCA

GGAAAGAAGTCACAGTGTTTACAGAAGTTCCGGTTCCTTTAACATTTGAA

AATGTAGTGCGGGCCACAGAGATCTCAAATCAAGCAATGTGCTGTT

---

What is claimed is:

1. An isolated nucleic acid construct comprising an RRK polynucleotide sequence, which is from between about 3100 and 6500 nucleotides in length and which hybridizes to SEQ ID NO:1 or to SEQ ID NO:3 under stringent conditions.

2. The nucleic acid construct of claim 1, wherein the RRK polynucleotide sequence encodes an RRK polypeptide comprising a leucine rich repeat motif.

3. The nucleic acid construct of claim 1, wherein the RRK polynucleotide sequence encodes an RRK polypeptide comprising a cytoplasmic protein kinase domain.

4. The nucleic acid construct of claim 1, wherein the polynucleotide sequence is a full length gene.

5. The nucleic acid construct of claim 1, wherein the RRK polynucleotide sequence is an Xa21 gene which encodes an Xa21 polypeptide as shown in SEQ ID NO:2.

6. The nucleic acid construct of claim 5, wherein the Xa21 polynucleotide sequence encodes an Xa21 polypeptide as shown in SEQ ID NO:4.

7. The nucleic acid construct of claim 5, wherein the Xa21 polynucleotide is as shown in SEQ ID NO:1.

8. The nucleic acid construct of claim 5, wherein the Xa21 polynucleotide is as shown in SEQ ID NO:3.

9. The nucleic acid construct of claim 1, further comprising a promoter operably linked to the RRK polynucleotide sequence.

10. The nucleic acid construct of claim 9, wherein the promoter is a tissue-specific promoter.

11. The nucleic acid construct of claim 9, wherein the promoter is a constitutive promoter.

12. A nucleic acid construct comprising a promoter sequence from an RRK gene linked to a heterologous polynucleotide sequence, wherein said promoter sequence is located upstream of a transcription site which corresponds to nucleotide 1644 of SEQ ID NO:1.

13. The construct of claim 12, wherein the heterologous polynucleotide sequence is a structural gene which confers pathogen resistance on plants.

14. The construct of claim 12, wherein the promoter is from SEQ ID NO:1.

15. A transgenic plant comprising a recombinant expression cassette comprising a plant promoter operably linked to a polynucleotide sequence of about 3100 to about 6500 nucleotides in length; wherein said polynucleotide sequence hybridizes to SEQ ID NO:1 or to SEQ ID NO:3 under stringent conditions.

16. The transgenic plant of claim 15, wherein the plant promoter is a heterologous promoter.

17. The transgenic plant of claim 15, wherein the plant is rice.

18. The transgenic plant of claim 15, wherein the plant is tomato.

19. The transgenic plant of claim 15, wherein the RRK polynucleotide sequence is an Xa21 polynucleotide which encodes an Xa21 polypeptide as shown in SEQ ID NO:2 or SEQ ID NO:4.

20. The transgenic plant of claim 19, wherein the polynucleotide sequence is as shown in SEQ ID NO:1 or in SEQ ID NO:3.

21. A method of enhancing resistance to Xanthomonas in a plant, the method comprising introducing into the plant a recombinant expression cassette comprising a plant promoter operably linked to an RRK polynucleotide sequence, which is between about 3100 and 6500 nucleotides in length and hybridizes to SEQ ID NO:1 or to SEQ ID NO:3 under stringent conditions.

22. The method of claim 21, wherein the plant tissue is from rice.

23. The method of claim 21, wherein the plant tissue is from tomato.

24. The method of claim 21, wherein the polynucleotide encodes an Xa21 polypeptide as shown in SEQ ID NO:2 or SEQ ID NO:4.

25. The method of claim 21, wherein the polynucleotide sequence is as shown in SEQ ID NO:1 or SEQ ID NO:3.

26. The method of claim 21, wherein the promoter is a tissue-specific promoter.

27. The method of claim 21, wherein the promoter is a constitutive promoter.

28. An isolated nucleic acid construct comprising an RRK polynucleotide sequence, which polynucleotide hybridizes to SEQ ID NO:24 under stringent conditions.

29. The isolated nucleic acid construct of claim 28, wherein the polynucleotide is as shown in SEQ ID NO:24.

30. An isolated nucleic acid construct comprising an RRK polynucleotide sequence, which polynucleotide hybridizes to SEQ ID NO:26 under stringent conditions.

31. The isolated nucleic acid construct of claim 30, wherein the polynucleotide is as shown in SEQ ID NO:26.

32. An isolated nucleic acid molecule which encodes a polypeptide comprising a sequence as shown in SEQ ID NO:2.

33. An isolated nucleic acid molecule which encodes a polypeptide comprising a sequence as shown in SEQ ID NO:4.

34. An isolated nucleic acid molecule which encodes a polypeptide comprising a sequence as shown in SEQ ID NO:25.

35. An isolated nucleic acid molecule which encodes a polypeptide comprising a sequence as shown in SEQ ID NO:27.

36. An isolated nucleic acid construct comprising a polynucleotide sequence which encodes an RRK disease resistance gene, wherein the construct remains hybridized to SEQ ID NOs:5, 7, 20, 21, 22 and 23 at a temperature of least 55° C. for at least 15 minutes.

37. The construct of claim 36, wherein the disease resistance gene is Xa21.

38. The construct of claim 36, wherein the polynucleotide is amplified from a cDNA library.

39. The construct of claim 36, wherein the plant is a tomato.

40. The construct of claim 36, wherein the polynucleotide is amplified using SEQ ID NO:22 and 23 as primers.

41. An isolated nucleic acid construct comprising a polynucleotide sequence which encodes an RRK disease resistance gene, wherein the polynucleotide is capable of being amplified from a plant cDNA or genomic library, the amplification comprising:

(i) a first amplification step of at least 20 amplification cycles wherein nucleic acids corresponding to SEQ ID NOs:5, 7, 20 and 21 are used as primers and annealing temperature is at least 55° C. for about 15 minutes; and (ii) a second amplification step of at least 30 amplification cycles wherein nucleic acids correspnding to SEQ ID NOs 22 and 23 are sued as primers and annealing temperature is at least 55° C. for about 15 minutes.

42. The construct of claim 36, wherein the disease resistance gene is Xa21.

43. The construct of claim 36, wherein the polynucleotide is amplified from a cDNA library.

44. The construct of claim 36, wherein the plant is a tomato.

45. The construct of claim 36, wherein the polynucleotide is amplified using SEQ ID NO:22 and 23 as primers.

* * * * *